United States Patent
Hanafusa et al.

(10) Patent No.: US 8,333,930 B2
(45) Date of Patent: Dec. 18, 2012

(54) REACTION KIT TREATING EQUIPMENT

(75) Inventors: Nobuhiro Hanafusa, Kyoto (JP); Koretsugu Ogata, Kyoto (JP); Koji Tanimizu, Kyoto (JP); Tomoichi Takahashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 806 days.

(21) Appl. No.: 12/279,830

(22) PCT Filed: Feb. 14, 2007

(86) PCT No.: PCT/JP2007/052568
§ 371 (c)(1),
(2), (4) Date: Aug. 18, 2008

(87) PCT Pub. No.: WO2007/097230
PCT Pub. Date: Aug. 30, 2007

(65) Prior Publication Data
US 2010/0213067 A1 Aug. 26, 2010

(30) Foreign Application Priority Data
Feb. 20, 2006 (JP) .................. 2006-043059

(51) Int. Cl.
*B01J 8/00* (2006.01)
(52) U.S. Cl. .......... 422/237; 422/602; 422/236; 222/52; 222/630
(58) Field of Classification Search .............. 222/52–57, 222/630–632; 422/601–603, 641–642, 236–237
See application file for complete search history.

(56) References Cited

U.S. PATENT DOCUMENTS 5,104,621 A * 4/1992 Pfost et al. ..................... 422/67
(Continued)

FOREIGN PATENT DOCUMENTS

JP 09-288080 A 11/1997
(Continued)

OTHER PUBLICATIONS

International Search Report for the Application No. PCT/JP2007/052568 mailed May 1, 2007.

*Primary Examiner* — J. Christopher Ball
(74) *Attorney, Agent, or Firm* — Cheng Law Group, PLLC

(57) ABSTRACT

Upper space on the front surface side of a reaction plate, provided with at least a reaction container causing reaction in a sample and a reagent container containing a reagent used for reaction with the sample, is covered with an airtight cover. A dispensation tip (20) for transporting liquid on the reaction plate is arranged in such a way that the distal end side is located on the inside of the covered space and the proximal portion is located on the outside. In order to handle a reaction kit (80) supported movably in the perpendicular direction and in the in-plane direction with respect to the front surface of the reaction plate, a table (82) for attaching the reaction kit (80), a drive unit (36) engaging with the proximal end of the dispensation tip (20) and driving the movement and the dispensation operation of the tip (20), a detection unit (38) for optically detecting a reaction product by receiving light generated through interaction with the reaction product on the reaction plate or the light generated from the reaction product, and a control section for controlling at least the dispensation operation by the drive unit (36) and the detection operation by the detection unit (38) are provided.

8 Claims, 20 Drawing Sheets

U.S. PATENT DOCUMENTS

| | | | |
|---|---|---|---|
| 6,627,446 B1* | 9/2003 | Roach et al. | 436/43 |
| 2003/0075557 A1* | 4/2003 | Deppe et al. | 222/54 |
| 2004/0002087 A1* | 1/2004 | Akahoshi et al. | 435/6 |
| 2004/0029260 A1* | 2/2004 | Hansen et al. | 435/287.2 |
| 2005/0106742 A1 | 5/2005 | Wahl | |

FOREIGN PATENT DOCUMENTS

| | | |
|---|---|---|
| JP | 2003-532120 A | 10/2003 |
| JP | 2005-130851 A | 5/2005 |
| JP | 2005-214710 A | 8/2005 |

* cited by examiner

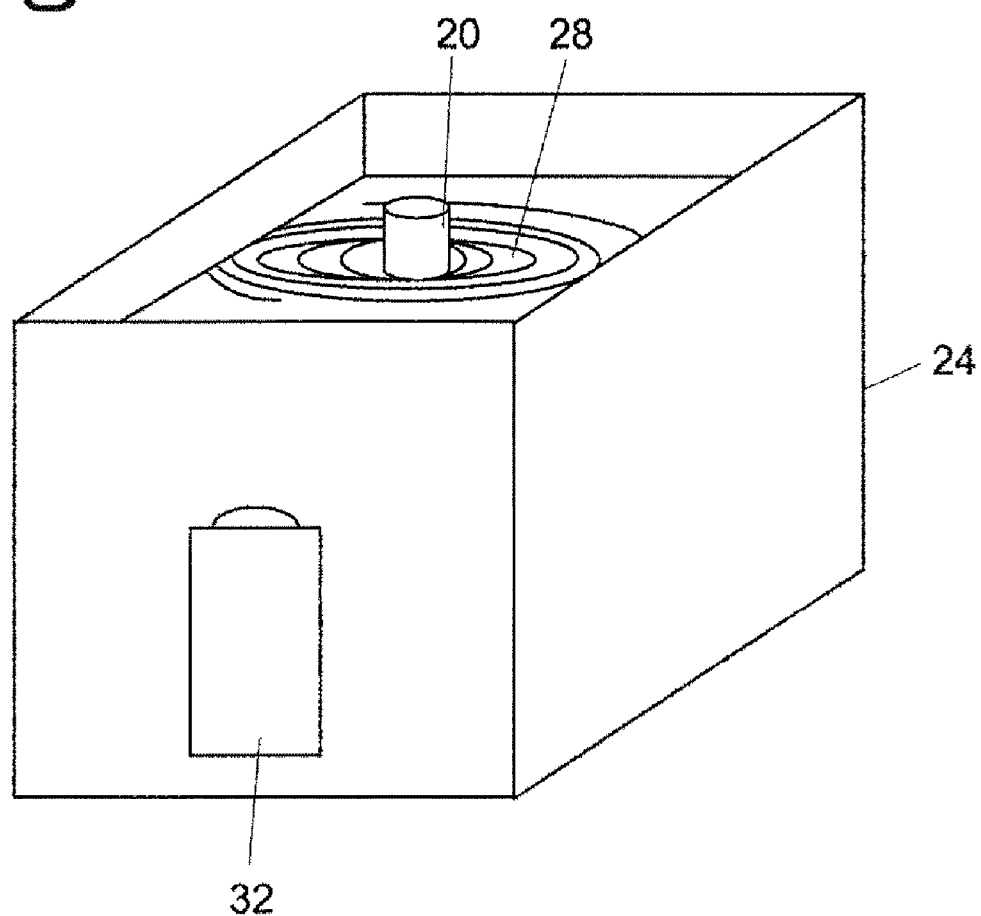

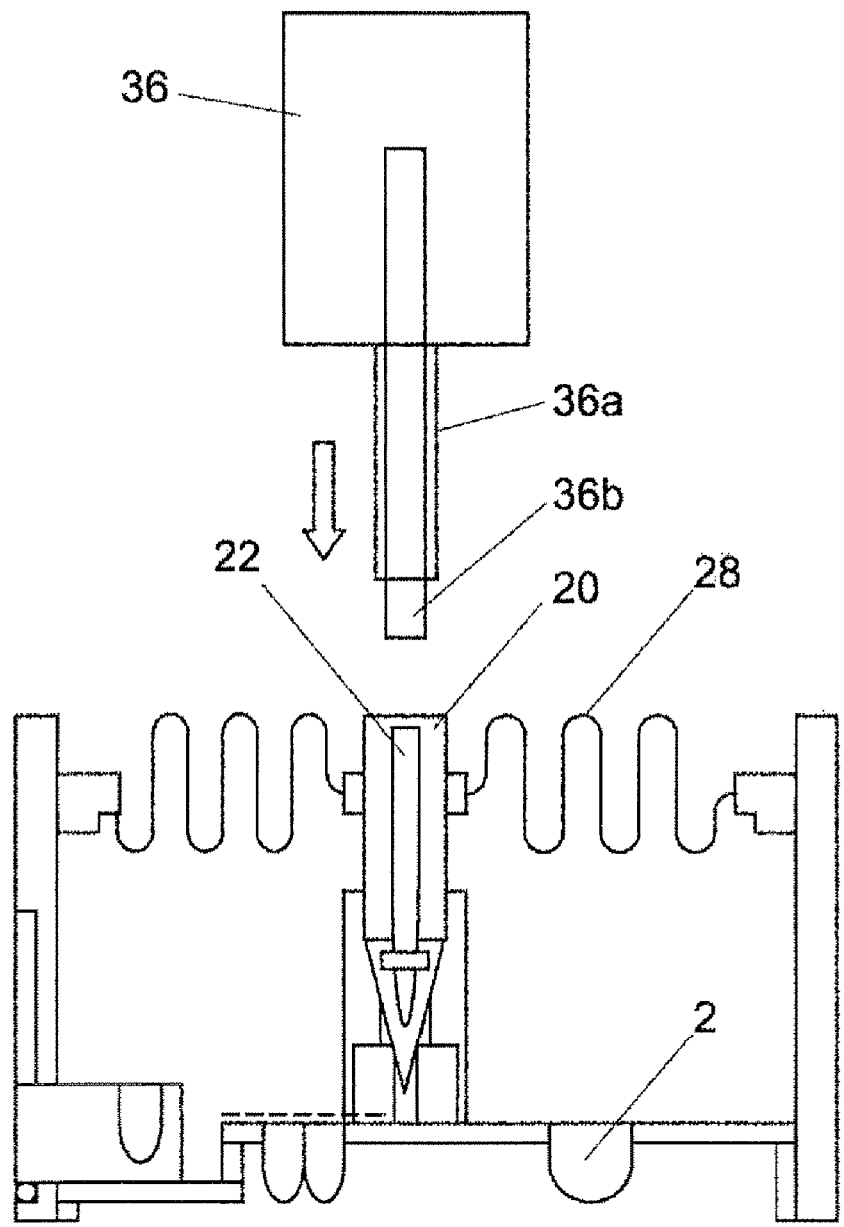

REACTION KIT TREATING EQUIPMENT

TECHNICAL FIELD

The present invention relates to reaction kit treatment equipment suitable for carrying out various analyses such as biological analyses, biochemical analyses, and general chemical analyses in the fields of medical care, chemistry, and the like.

BACKGROUND ART

In biochemical analyses, general chemical analyses, and the like, micro multi-chamber devices are used as small-size reaction devices. As such a device, for example, a microwell reaction plate such as a microtiter plate, which has a flat plate substrate with a plurality of wells on the surface of the substrate, are used.

DISCLOSURE OF THE INVENTION

Problems to be Solved by the Invention

In the case of a conventional microwell reaction plate, the top surface of the reaction plate is exposed to ambient air during use. Therefore, there is a fear that foreign matter will enter a sample from the outside, and on the other hand, there is a possibility that a reaction product will pollute a surrounding environment.

It is therefore an object of the present invention to provide reaction kit treatment equipment for carrying out an analysis using a reaction kit capable of preventing the entry of foreign matter from the outside into a reaction plate and the pollution of a surrounding environment.

Means for Solving the Problems

The present invention is directed to reaction kit treatment equipment for treating a reaction kit which includes a reaction plate having at least a reaction container for carrying out the reaction of a sample, an airtight cover for covering a space above the top surface of the reaction plate, and a dispensation tip arranged so that a distal end side thereof is located inside the space covered with the cover and a proximal end thereof is located outside the space to transfer liquid over the reaction plate, the dispensation tip being supported movably in an in-plane direction parallel to the top surface of the reaction plate and in a direction perpendicular to the top surface. The reaction kit treatment equipment includes a reaction kit attachment section for attaching the reaction kit, a drive unit for engaging with the proximal end of the dispensation tip, moving and driving the dispensation tip to carry out dispensation operation, means for detecting a reaction product contained in the reaction plate, and a control section for controlling at least the dispensation operation carried out by the drive unit and the detection carried out by the detection means.

Since the space above the top surface of the reaction plate is covered with the cover so as to be cut off from an outside environment, the reaction of a sample is carried out in the space. The analysis of a reaction product obtained by the reaction is also carried out in the space covered with the cover without transferring the reaction product to the outside of the cover. After the completion of the analysis, the reaction kit is disposed of with the reaction product remaining in the space covered with the cover. That is, the reaction kit is disposable.

The dispensation tip may be one to be attached to the tip of a dispensation nozzle. In this case, it is necessary to separately provide a nozzle mechanism to carry out dispensation operation. Therefore, for the purpose of eliminating the necessity to provide a nozzle mechanism, the dispensation tip, in a preferred embodiment of the present invention, has a syringe driven from the outside of the cover to carry out dispensation operation. In this case, the drive unit drives the syringe to carry out dispensation operation.

There is a case where the reaction plate needs to carry out temperature control during reaction or analysis. For example, in a case where the reaction kit is intended for use in gene analysis, there is a case where it has a gene amplification section for carrying out gene amplification reaction on the top surface side of the reaction plate. Examples of gene amplification reaction include PCR, LAMP, and the like, and the temperature of the gene amplification section is controlled according to a predetermined temperature cycle. Further, there is a case where it is necessary to carry out temperature control also during analysis. For this reason, the reaction kit treatment equipment may further include a temperature control unit for controlling the temperature of the reaction plate during reaction and/or analysis.

One embodiment of the detection means includes an absorbance detector provided with an irradiation optical system for irradiating a reaction product with measuring light from the outside of the reaction plate and a light-receiving optical system for receiving and detecting the measuring light having absorbed by the reaction product.

Another embodiment of the detection means includes a fluorescence detector provided with an excitation optical system for irradiating a reaction product with excitation light from the outside of the reaction plate and a light-receiving optical system for receiving and detecting fluorescence emitted from the reaction product excited by the excitation light.

Another embodiment of the detection means includes an emission detector arranged outside the reaction plate and provided with a light-receiving optical system for receiving and detecting light emitted from a reaction product.

Another embodiment of the detection means is one to be used when the reaction plate has an electrophoresis section for analyzing a reaction product by electrophoretic separation. This detection means has a power supply for applying an electrophoresis voltage to the electrophoresis section and an optical detector for optically detecting the components of a reaction product separated by the electrophoresis section.

Another embodiment of the detection means is one to be used when the reaction plate has a probe region where probes to be reacted with a gene are arranged to analyze a reaction product. This detection means has an optical detector for optically detecting the components of a reaction product bound to the probes arranged in the probe region.

Another embodiment of the detection means is one to be used when the reaction plate has a probe region where probes to be reacted with a gene are arranged to analyze a reaction product. This detection means has a detector for electrically detecting the components of a reaction product bound to the probes arranged in the probe region.

Examples of such a probe region include DNA chips and hybridization regions.

The reaction kit handled in the reaction kit treatment equipment is used for measuring various reactions such as chemical reactions and biochemical reactions. Examples of a sample measured using such a reaction kit include, but are not limited to, chemical substances, biological samples, living body-derived samples, and the like.

Effect of the Invention

By handling the reaction kit in the reaction kit treatment equipment according to the present invention, it is possible to use the reaction kit with a space above the top surface of the reaction plate being covered with the cover, thereby preventing both the entry of foreign matter from the outside into a sample and the pollution of an outside environment with a reaction product.

Further, in a case where the dispensation tip has a syringe driven from the outside of the cover, it is possible to eliminate the necessity to separately provide a nozzle mechanism in the reaction kit treatment equipment according to the present invention.

Even when the dispensation tip does not have a syringe, in a case where the dispensation tip has a filter in the tip portion thereof, it is possible to prevent the entry of foreign matter from the outside through the dispensation tip, and it is also possible to prevent the release of a reaction product into an outside environment through the dispensation tip and thus to prevent the pollution of an outside environment with the reaction product.

In the case of carrying out gene amplification reaction, there is a problem that other DNA or the like will enter a sample from the outside. Further, there is also a problem that other samples will be contaminated with an amplified gene. However, in the present invention, gene amplification reaction can be carried out in an enclosed space, thereby preventing a sample from being contaminated from the outside. In addition, the reaction kit with a reaction product being trapped in the enclosed space can be disposed of after the completion of the analysis of the reaction product, thereby eliminating the fear that other samples will be contaminated.

Further, by allowing the detection means to have an optical detector including an absorbance detector, a fluorescence detector, or an emission detector, an optical detector for an electrophoresis section, an optical or electrical detector for a probe region, or the like, it is possible to easily detect a reaction product from the outside of the reaction kit handled in the reaction kit treatment equipment while the reaction kit is kept hermetically sealed.

BRIEF DESCRIPTION OF THE DRAWINGS

FIG. 2 is a perspective view showing the appearance of the same reaction kit as in FIG. 1A.

FIG. 3 is a vertical sectional view showing a state after a sample is introduced into the reaction kit.

Figure 1A:
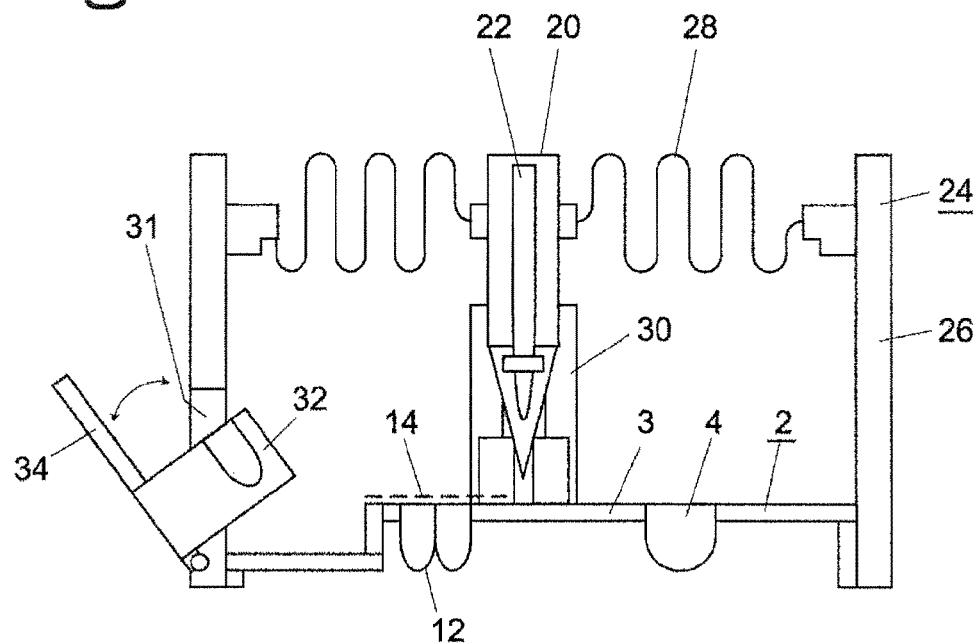
FIG. 1A is a vertical sectional view of one example of a reaction kit handled in a reaction kit treatment equipment according to the present invention.

DESCRIPTION OF THE REFERENCE NUMERALS 2, 2a, 2b, 2c reaction plate
3 substrate 4 reaction container
12 reagent container
14 film
20 dispensation nozzle
22 plunger of syringe
23 filter
24 cover
26 cover main body
28 bellows film
32, 32a sample container
36 drive unit
38 detection unit
64, 64a, 71 cover plate
66, 68, 72 sealant
80 reaction kit
82 table
83 temperature control unit
84 control section
86 personal computer
100, 110, 120 DNA chip
106 electrode
102 electrophoretic separation channel

BEST MODE FOR CARRYING OUT THE INVENTION

Figure 1B:
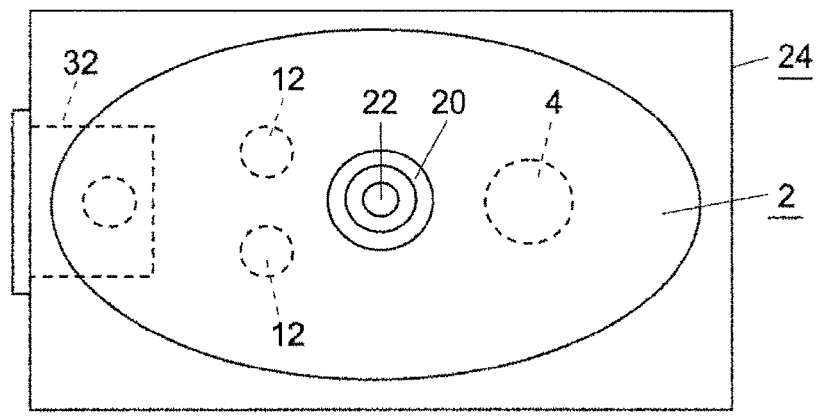
FIG. 1B is a plan view showing one example of a reaction plate and a dispensation tip of the reaction kit handled in a reaction kit treatment equipment according to the present invention.

FIG. 1A is a vertical sectional view of a reaction kit handled in a reaction kit treatment equipment according to the present invention, FIG. 1B is a plan view showing a reaction plate and a dispensation tip 20 of the reaction kit, and FIG. 2 is a perspective view of the reaction kit.

As shown in FIG. 1, the reaction plate 2 has a reaction container 4 for carrying out reaction of a sample and reagent containers 12 for receiving reagents used for the reaction of the sample on the top surface of a substrate 3. Each of the reagent containers 12 is sealed with a film 14.

The reaction container 4 is provided as a recess in the top surface of the substrate 3. In a case where the reaction container 4 is intended for reaction carried out under externally-controlled temperature conditions, a part of the reaction container 4 subjected to temperature control preferably has a small thickness to enhance heat conductivity.

Each of the reagent containers 12 is also provided as a recess in the top surface of the substrate 3, and contains a reagent to be used for reaction, and is covered with the film 14 through which the dispensation tip 20 (which will be described later) can pass. Examples of such a film 14 include an aluminum foil and a laminated film having an aluminum film and a resin film such as a PET (polyethylene terephthalate) film. The film 14 is attached by welding or adhesion so as not to be easily detached.

If necessary, a mixing chamber for mixing a sample with a reagent may be provided as a recess in the top surface of the substrate 3. Further, such a mixing chamber may be covered with the film 14 with its recess being empty.

The reaction container 4 may be used as a detection chamber for detecting a reaction product formed in the reaction container 4. In this case, detection of a reaction product can be carried out by, for example, means for externally irradiating the reaction container 4 with light. Alternatively, a detection chamber may be provided separately from the reaction container 4. For example, in a case where a plurality of detection chambers are provided separately from the reaction container 4, the detection chambers may previously contain different reagents for detecting the state of a reaction mixture obtained by the reaction of a sample with a reagent, and the reaction mixture is dispensed into the detection chambers by the dispensation tip 20. The opening of such a detection chamber may be covered with a film through which the dispensation tip 20 can pass. As in the case of the film 14, examples of the film for covering the detection chamber include an aluminum foil and a laminated film having an aluminum film and a resin film such as a PET film, and the film can be attached by welding or adhesion so as not to be easily detached.

The material of the substrate 3 having the reaction container 4 is not particularly limited, but is preferably cheaply available because the reaction kit is disposable. Preferred examples of such a material include resin materials such as polypropylene and polycarbonate. In a case where the reaction kit is designed to allow a reaction product to be detected by absorbance, fluorescence, chemiluminescence, or bioluminescence in the reaction container 4 or a detection chamber provided separately from the reaction container 4, the substrate 3 is preferably made of an optically-transparent resin so that the reaction product can be optically detected from the bottom surface side of the substrate 3. Particularly, in a case where a reaction product is detected by fluorescence, the substrate 3 is preferably made of a low self-fluorescence (i.e., the amount of fluorescence emitted from a material itself is small) and an optically-transparent resin such as polycarbonate. The thickness of the substrate 2 is in the range of 0.3 to 4 mm, preferably in the range of 1 to 2 mm. From the viewpoint of low self-fluorescence, the thickness of the substrate 3 is preferably small.

The dispensation tip 20 is arranged above the top surface of the reaction plate 2. The dispensation tip 20 is used to dispense a sample and a reagent. Further, in a case where the reaction plate 2 has a detection chamber provided separately from the reaction container 4, the dispensation tip 20 is used also to dispense a reaction mixture obtained by reacting a sample with a reagent into the detection chamber. The dispensation tip 20 has a syringe 22, and the syringe 22 is driven from the outside of a cover 24 to carry out dispensation operation.

Figure 1C:
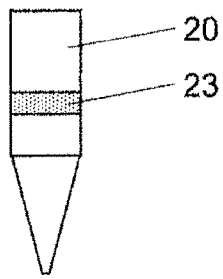
FIG. 1C is a sectional view schematically showing another example of the dispensation tip in the reaction kit handled in a reaction kit treatment equipment according to the present invention.

As shown in FIG. 1C, the dispensation tip 20 may have a filter 23 in its inside instead of the syringe 22. The filter adsorbs foreign matter entering from the outside, and is therefore more effective to prevent the entry of foreign matter into a space covered with the cover 24 and to prevent the release of reactants and a reaction product from the space covered with the cover 24 into the outside.

The cover 24 is provided so as to cover a space above the top surface of the reaction plate 2. The cover 24 includes a cover main body 26 for covering the periphery of the reaction plate 2 and a bellows film 28 for covering the top of the reaction plate 2 so that a space above the top surface of the reaction plate 2 is cut off from the outside. The cover main body 26 is provided integrally with the reaction plate 2 by fixing the lower end of the cover main body 26 to the reaction plate 2 or by using a sealant provided between the lower end of the cover main body 26 and the reaction plate 2, and has stiffness to maintain the shape of the cover 24. The bellows film 28 is formed from a flexible diaphragm or a flexible film, and movably holds the dispensation tip 20 so that a distal end thereof is located inside a space covered with the cover 24 and a proximal end thereof is located outside the space covered with the cover 24.

The material of the cover 24 is not particularly limited as long as it can cover a space above the top surface of the reaction plate 2 while keeping the reaction kit hermetically sealed. However, the cover 24 is preferably made of a cheaply-available material because the reaction kit is disposable. Preferred examples of a material for forming the cover main body 26 include resin materials such as polypropylene and polycarbonate, and preferred examples of a material for forming the bellows film 28 include Nylon®, polyvinyl chloride, and rubber materials such as silicone rubber and the like.

A holding member 30 for holding the dispensation tip 20 before and after its use is provided on the cover main body 26 or the substrate 3. When used for dispensation operation, the dispensation tip 20 is detached from the holding member 30 so as to be freely moved over the top surface of the reaction plate 2.

The cover main body 26 has an opening 31 for supplying a sample onto the reaction plate 2 from the outside of the cover 24. Further, a sample container 32 is openably and closably attached to the opening 31. The sample container 32 has a recess for receiving a sample, and the recess has an opening formed in the top surface of the sample container 32. After a sample is injected into the recess and is then placed inside the cover 24, the opening 31 is hermetically sealed by bringing a plate 34 holding the sample container 32 into intimate contact with the cover main body 26 using a pressure-sensitive adhesive applied onto the inner surface of the plate 34 or by engaging the plate 34 with the cover main body 26 with a sealant interposed therebetween. That is, the opening 31 is an opening hermetically sealable.

The reaction kit is disposable, and is therefore entirely disposed of without removing the cover 24 from the reaction plate 2 after the completion of analysis of one sample.

Hereinafter, the operation of analyzing a sample with the reaction kit will be described.

Prior to analysis, a sample is injected into the sample container 32 through the opening 31, and then the opening 31 is closed by the sample container 32, and therefore the sample container 32 is fixed to the cover main body 26. As a result, the sample is placed in a space covered with the cover 24 of the reaction kit and is cut off from the outside.

After the sample is introduced into the reaction kit, as shown in FIG. 3, engagement of a drive unit 36 with the dispensation tip 20 and the syringe 22 is allowed to start.

Figure 4:
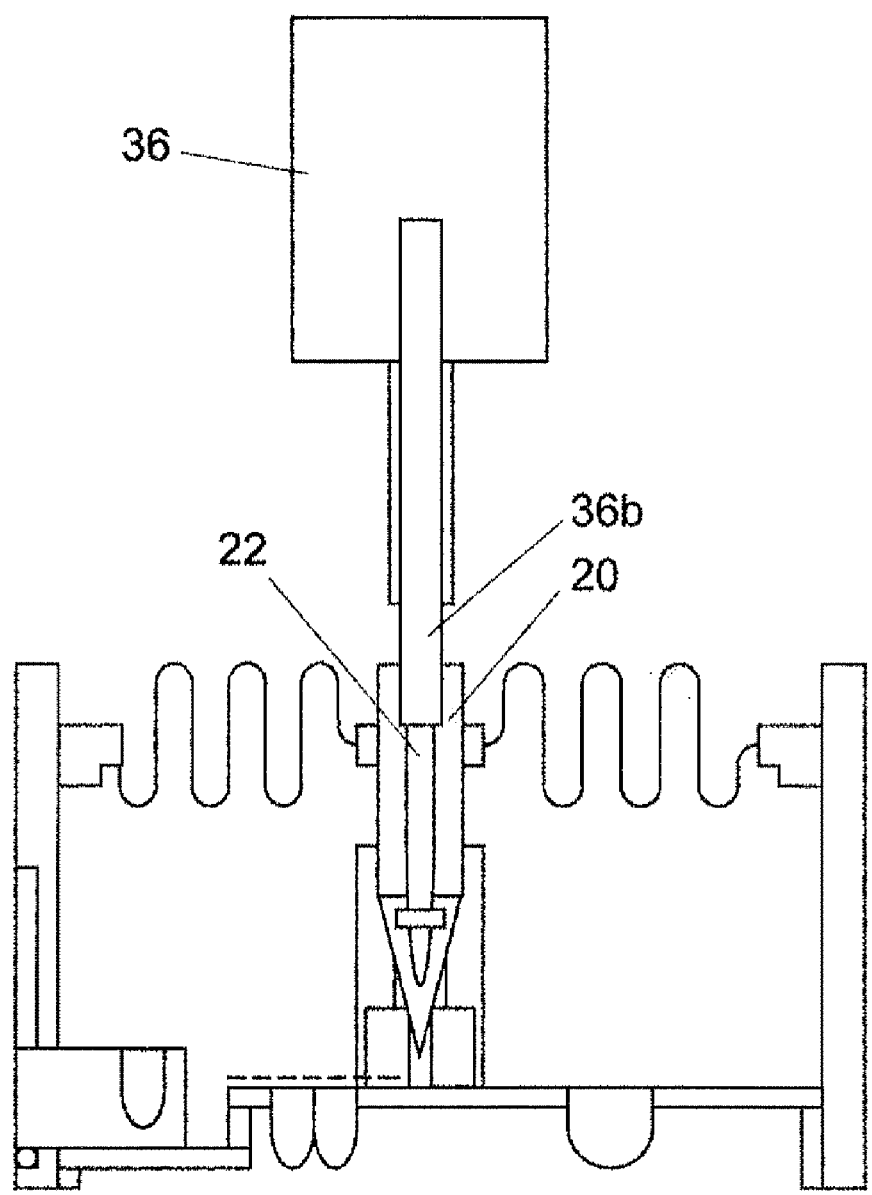
FIG. 4 is a vertical sectional view showing a state after a syringe drive section of a drive unit is engaged with a plunger of a syringe in the reaction kit.

First, as shown in FIG. 4, a plunger holder 36b as a syringe drive section is moved down to be engaged with a plunger of the syringe 22.

Figure 5:
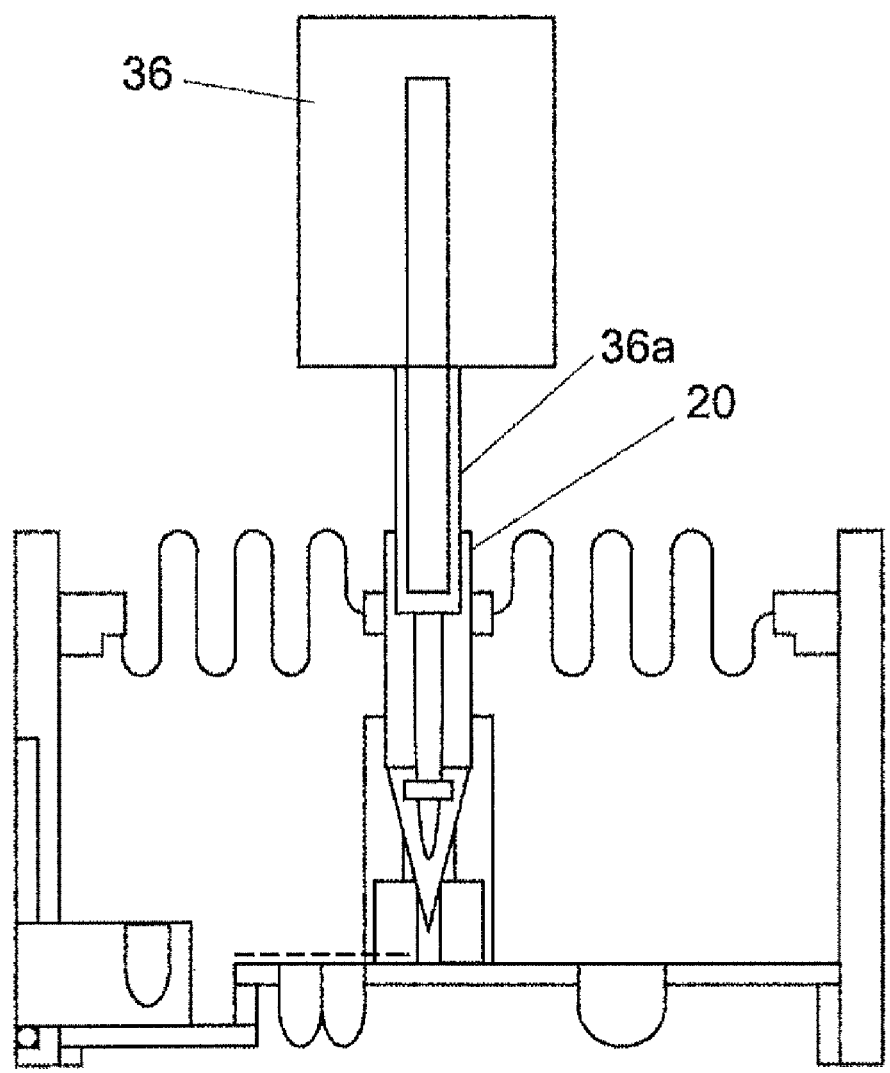
FIG. 5 is a vertical sectional view showing a state after a tip holding section of the drive unit is engaged with the dispensation tip in the reaction kit.

Then, as shown in FIG. 5, a tip holder 36a is also moved down to be press-fitted to the dispensation tip 20 so that the dispensation tip 20 is held by the tip holder 36a.

Figure 6:
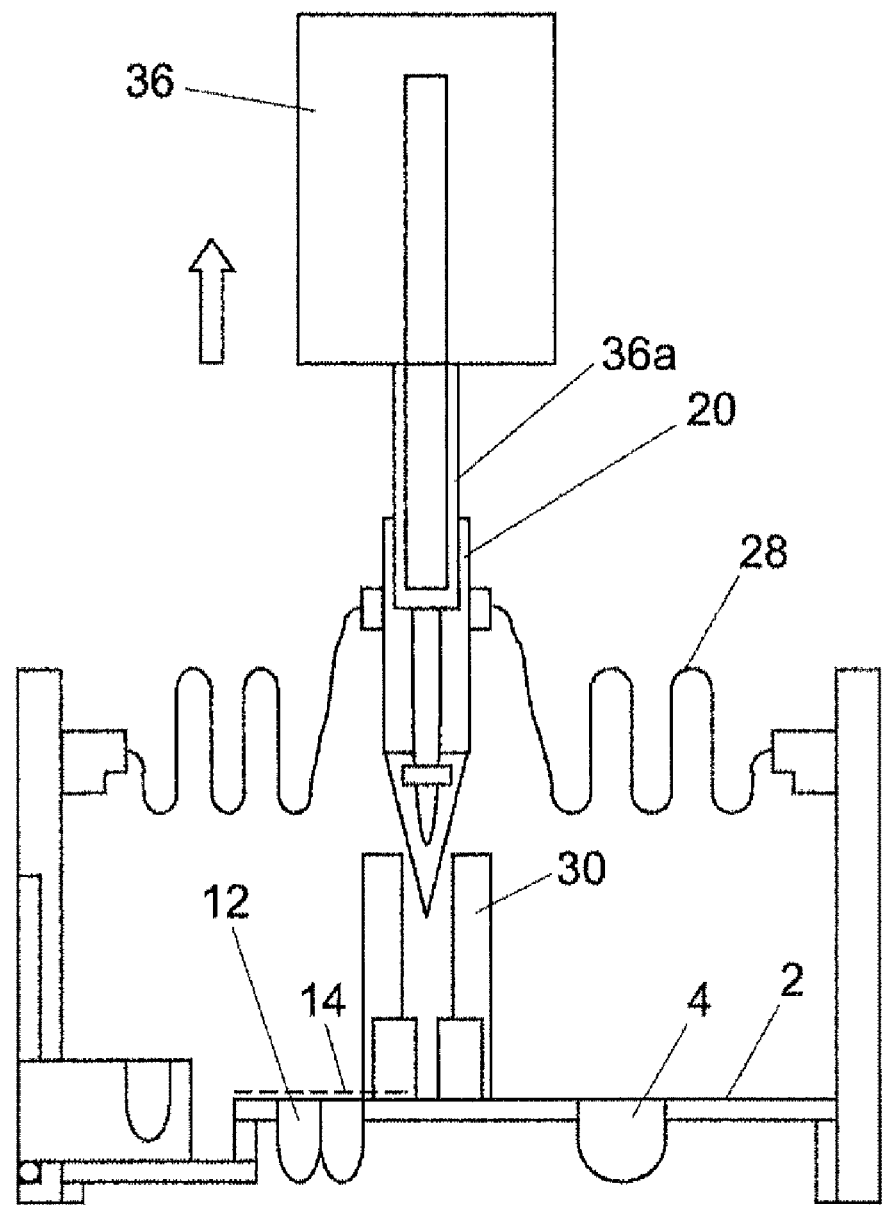
FIG. 6 is a vertical sectional view showing a state after the dispensation tip is detached from the holding section in the reaction kit.

Next, as shown in FIG. 6, the dispensation tip 20 is detached from the holding section 30. In this way, the dispensation tip 20 becomes able to be freely moved by the bellows film 28 with its distal end being cut off from the outside.

The dispensation tip 20 is moved to the sample container 32 to take a sample, and then the sample is dispensed into the reaction container 4 by the dispensation tip 20.

Then, the dispensation tip 20 is moved to the reagent container 12, and the distal end of the dispensation tip 20 is passed through the film 14 to take a reagent from the reagent container 12, and the reagent is dispensed into the reaction container 4 by the dispensation tip 20 to react the sample with the reagent. If necessary, the reaction container 4 is brought into contact with an external heat source during the reaction to adjust the temperature of the reaction container 4 to a predetermined temperature.

During or after the reaction, detection of a reaction product is carried out. In this case, it is assumed that a reaction product contained in the reaction container 4 is optically detected from the outside of the reaction plate 2. Therefore, a detection unit is arranged below the reaction container 4 to detect a reaction product by optical means or other means.

As described above, the reaction plate 2 of the reaction kit has reagent containers 12, but the reagent containers 12 can be omitted from the reaction plate 2. In this case, both a sample and a reagent may be injected into the sample container 32 to introduce them into the reaction kit, or another container not shown may be used to introduce a reagent into the reaction kit.

Figure 7:
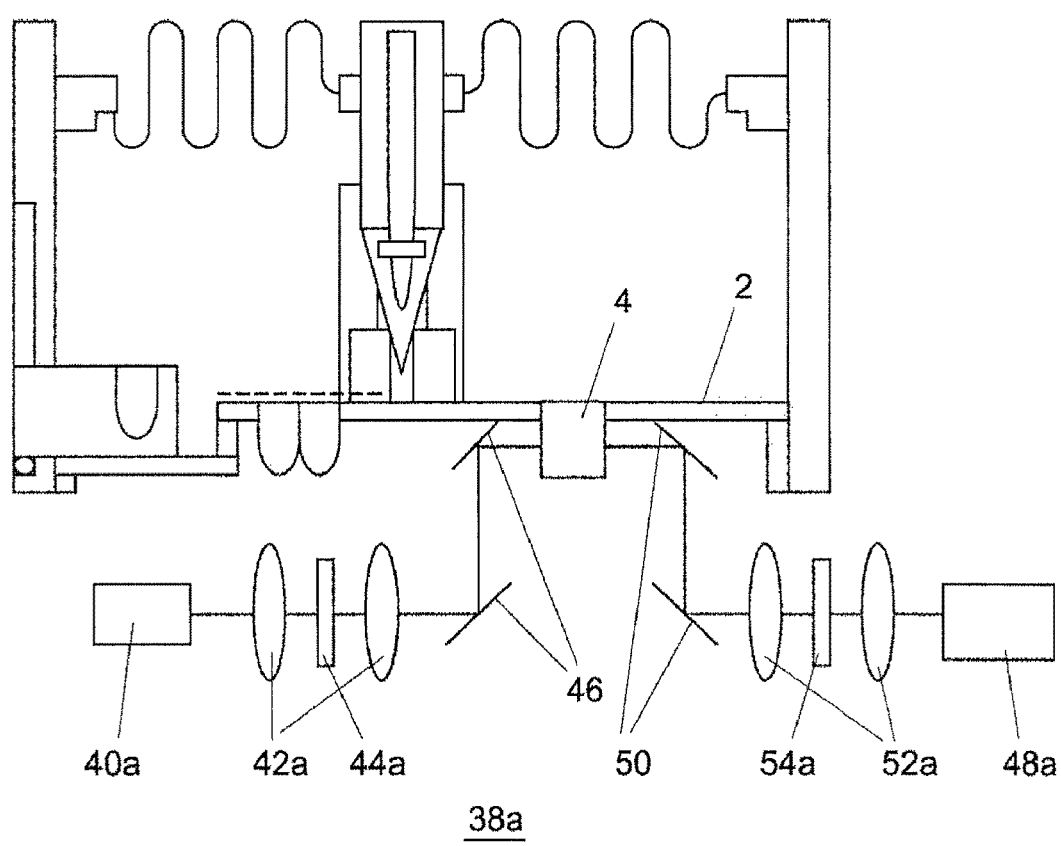
FIG. 7 is a vertical sectional view showing a first example of a detection unit used for the detection of a reaction product in the reaction kit treatment equipment according to the present invention.
Figure 8:
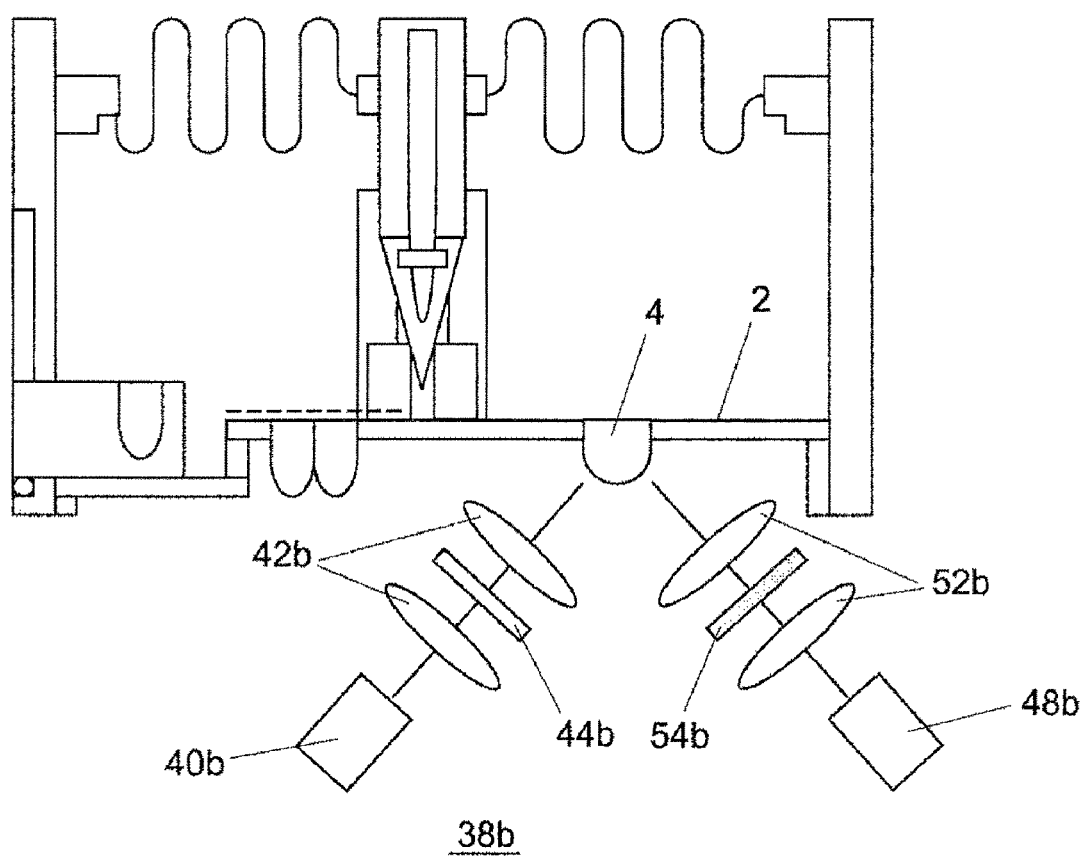
FIG. 8 is a vertical sectional view showing a second example of the detection unit used for the detection of a reaction product in the reaction kit treatment equipment according to the present invention.
Figure 9:
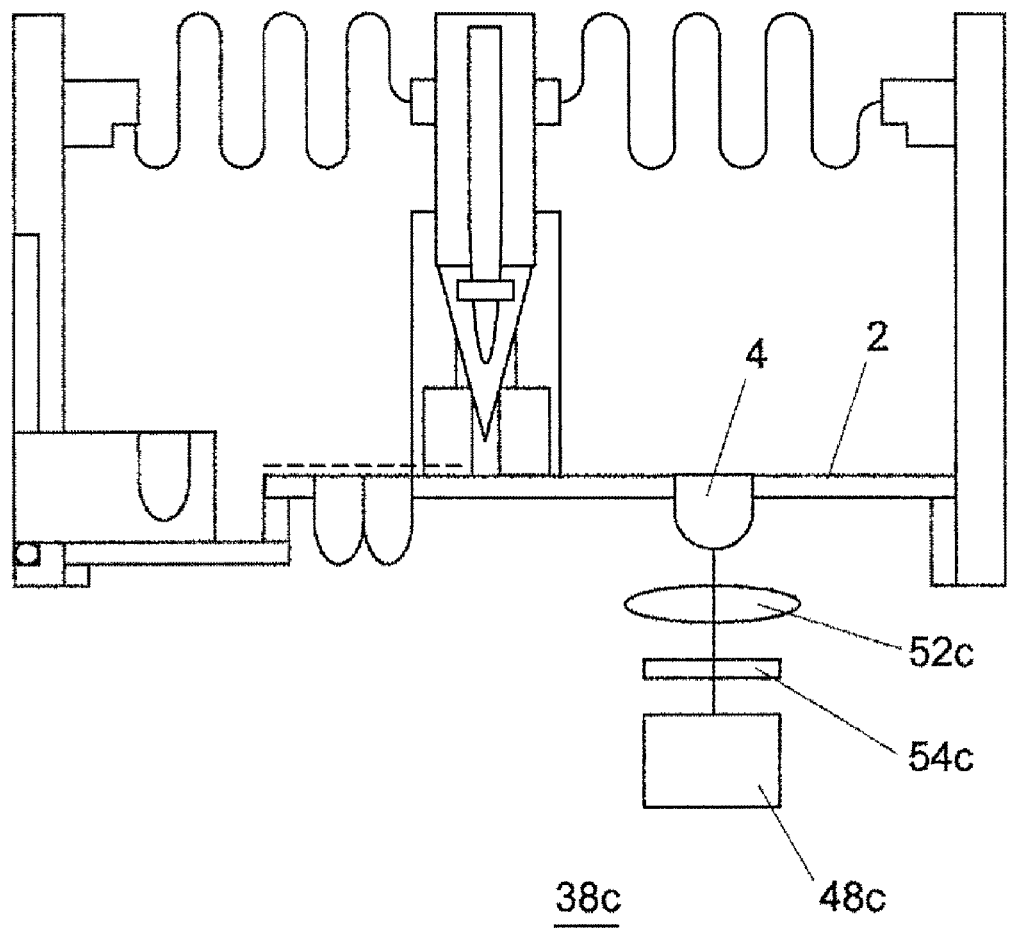
FIG. 9 is a vertical sectional view showing a third example of the detection unit used for the detection of a reaction product in the reaction kit treatment equipment according to the present invention.

FIGS. 7 to 9 show examples of a detection unit provided as detection means in the reaction kit treatment equipment according to the present invention to detect a reaction product.

FIG. 7 shows an example of the detection unit including an absorbance detector. In this case, the reaction container 4 preferably has a pair of parallel flat surfaces serving as a light incident surface through which measuring light enters and a light exiting surface through which measuring light exits.

A detection unit 38a includes an irradiation optical system. The irradiation optical system has, on its optical path, a light source 40a, a pair of lenses 42a for once condensing light emitted from the light source 40a to obtain parallel light and then condensing the parallel light to irradiate the reaction container 4 with condensed light, a filter 44a arranged between the pair of lenses 42a at a position where the parallel light travels to select light having a predetermined wavelength from light emitted from the light source 40a to obtain measuring light, and mirrors 46 for guiding the measuring light to the light incident surface of the reaction container 4. As the light source 40a, a lamp light source such as a tungsten lamp which emits light having wavelengths ranging from the ultraviolet light region to the visible light region, a light-emitting diode (LED), a laser diode (LD), or the like is used. Further, the detection unit 38a includes a light-receiving optical system. The light-receiving optical system has, on its optical path, a photodetector 48a, mirrors 50 for guiding light exiting from the reaction container 4 through its light exiting surface to the photodetector 48a, a pair of lenses 52 for once converting the light into parallel light and then condensing the parallel light to introduce condensed light into the photodetector 48a, and a filter 54a arranged between the pair of lenses 52 at a portion where the parallel light travels to select light having a predetermined wavelength suitable for measurement.

The reason for once converting light into parallel light by the lenses 42a and 52a is to improve the precision of wavelength selection by the filters 44a and 54a.

In the case of using such a detection unit 38a, light having a wavelength suitable for detecting a reaction product is selected from light emitted from the light source 40a by the filters 44a and 54a, and absorbance is measured at the selected wavelength to detect the reaction product.

FIG. 8 shows an example of a detection unit including a fluorescence detector.

A detection unit 38b includes an excitation optical system. The excitation optical system has a light source 40b, a pair of lenses 42b for once condensing light emitted from the light source 40b to obtain parallel light and then condensing the parallel light to irradiate the reaction container 4 with condensed light, and a filter 44b arranged on the optical path of parallel light beams obtained by the lens 42b to select light having a predetermined excitation wavelength from light emitted from the light source 40b. Further, the detection unit 38b includes a light-receiving optical system. The light-receiving optical system has a photodetector 48b, a pair of lenses 52b for receiving fluorescence emitted from the reaction container 4, once converting the fluorescence into parallel light, and condensing the parallel light to introduce condensed light into the photodetector 48b, and a filter 54b arranged on the optical path of the parallel fluorescence beams obtained by the lens 52b to select light having a predetermined fluorescence wavelength. Similarly, the reason for once converting light into parallel light by the lenses 42b and 52b is to improve the precision of wavelength selection by the filters 44b and 54b.

In the case of using such a detection unit 38b, light having an excitation wavelength for exciting a reaction product is selected from light emitted from the light source 40b by the filter 44b to irradiate the reaction product contained in the reaction container 4 with the selected light, and fluorescence emitted from the reaction product is received by the light-receiving optical system, and light having a predetermined fluorescence wavelength is selected by the filter 54b, and the selected fluorescence is detected by the photodetector 48b.

FIG. 9 shows an example of the detection unit for detecting chemiluminescence or bioluminescence emitted from a reaction product.

A detection unit 38c has a photodetector 48c for detecting light emitted from the reaction container 4, a lens 52c for receiving light emitted from the reaction container 4 and guiding condensed light to the photodetector 48c, and a filter 54c for selecting light having a predetermined emission wavelength from the condensed light.

In the case of using such a detection unit 38c, chemiluminescence or bioluminescence emitted from a reaction product contained in the reaction container 4 is condensed by the lens 52c, and light having a predetermined emission wavelength is selected by the filter 54c, and the selected light is detected by the photodetector 48c.

FIGS. 10 to 14 show other reaction kits different in the structure of the reaction plate. The reaction plate of the reaction kit described above is designed to allow a reaction product to be detected in the reaction container 4, but the reaction plate of each of the reaction kits shown in FIGS. 10 to 14 further has an analysis section for analyzing a reaction product.

Figure 10A:
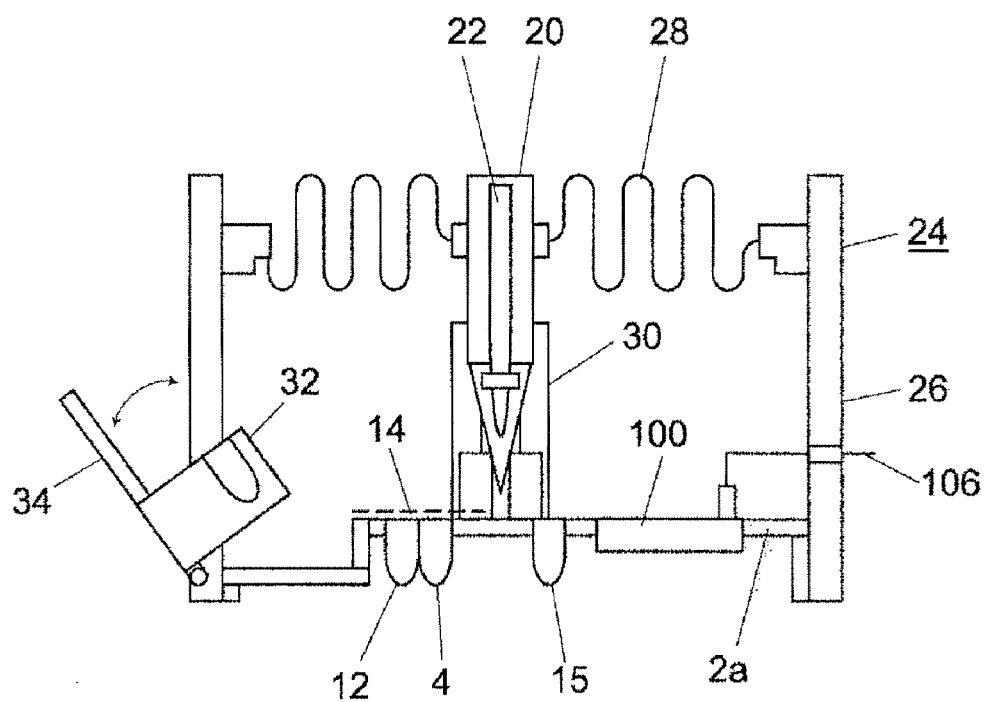
FIG. 10A is a vertical sectional view of another example of the reaction kit.
Figure 10B:
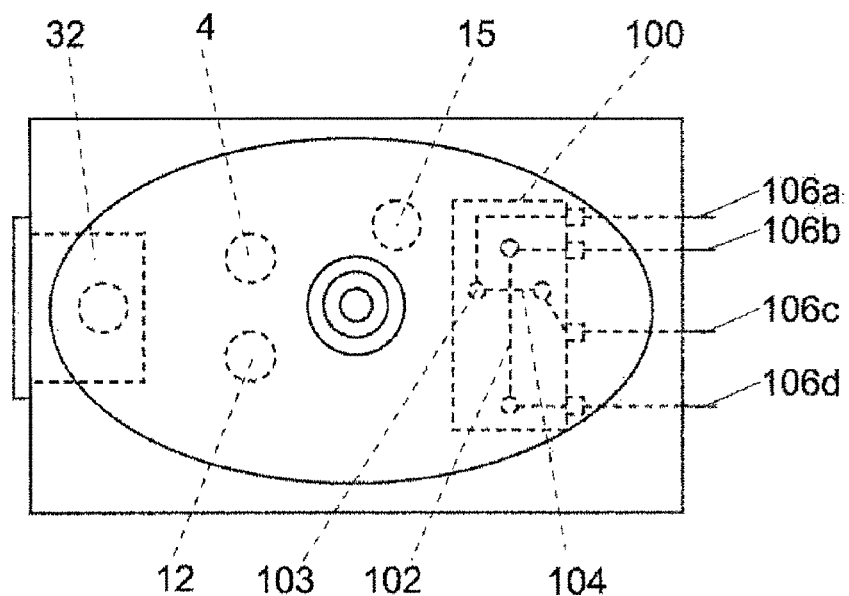
FIG. 10B is a plan view showing a reaction plate and a dispensation tip of the reaction kit shown in FIG. 10A.

A reaction plate 2a of the reaction kit shown in FIG. 10 has an electrophoresis section as the analysis section. In this case, an electrophoresis chip 100 is used as one example of the electrophoresis section. The electrophoresis chip 100 has a reaction product injection section 103, an electrophoretic separation channel 102, and electrodes 106a to 106d for applying an electrophoresis voltage. The electrophoresis chip 100 further has, in addition to the electrophoretic separation channel 102, a sample introduction channel 104 arranged so as to cross the channel 102 to introduce a sample into the channel 102, but the sample introduction channel 104 may have such a structure that a sample can be directly introduced thereinto from one end of the channel 102. The electrophoresis chip 100 is subjected to fluorescence detection from the back surface side thereof, and is therefore made of a low self-fluorescence and an optically-transparent resin such as polycarbonate, glass, or quartz.

The reaction plate 2a further has a separation buffer container 15 provided in the top surface thereof to receive a separation buffer to be injected into the channels 102 and 104. The separation buffer container 15 is sealed with a film through which the tip of the dispensation tip 20 can pass.

The electrodes 106a to 106d for applying an electrophoresis voltage are connected to both ends of the channel 102 and 104, respectively. These electrodes 106a to 106d are extended to the outside of the cover 24 so as to be connected to a power supply provided outside the reaction kit.

Each of the channels 102 and 104 has a reservoir at its end, and a separation buffer contained in the separation buffer container 15 is injected into the reservoirs.

In a case where the reaction kit is used for gene analysis, the reagent container 12 is allowed to previously contain a PCR reaction reagent. In this case, the reaction container 4 serves as a PCR reaction container.

In a case where a gene sample is measured using the reaction kit, a sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered over a mixture of the sample and the reagent contained in the reaction container 4, and then PCR reaction is carried out by controlling the temperature of the reaction mixture contained in the reaction container 4 according to a predetermined temperature cycle.

A separation buffer is supplied by the dispensation tip 20 from the separation buffer container 15 to the channels 102 and 104 through the reservoirs in the electrophoresis chip 100.

After the completion of the PCR reaction, an obtained reaction mixture is supplied as a sample by the dispensation tip 20 from the reaction container 4 to the injection section 103 of the electrophoresis chip 100 having the separation buffer previously supplied. Then, a voltage is applied from a power supply 101 (see FIG. 11) provided in the reaction kit treatment equipment to the channels 102 and 104 through the electrodes 106a to 106d to introduce the sample into the electrophoretic separation channel 102, and then the sample is electrophoresed in the channel 102 to be separated into its components.

In order to detect sample components separated by electrophoresis, the reaction kit treatment equipment has a detection unit 38d.

It is to be noted that in this case, the reaction container 4 is used as a PCR reaction container, but a PCR reaction container may be provided separately from the reaction container 4.

Figure 11:
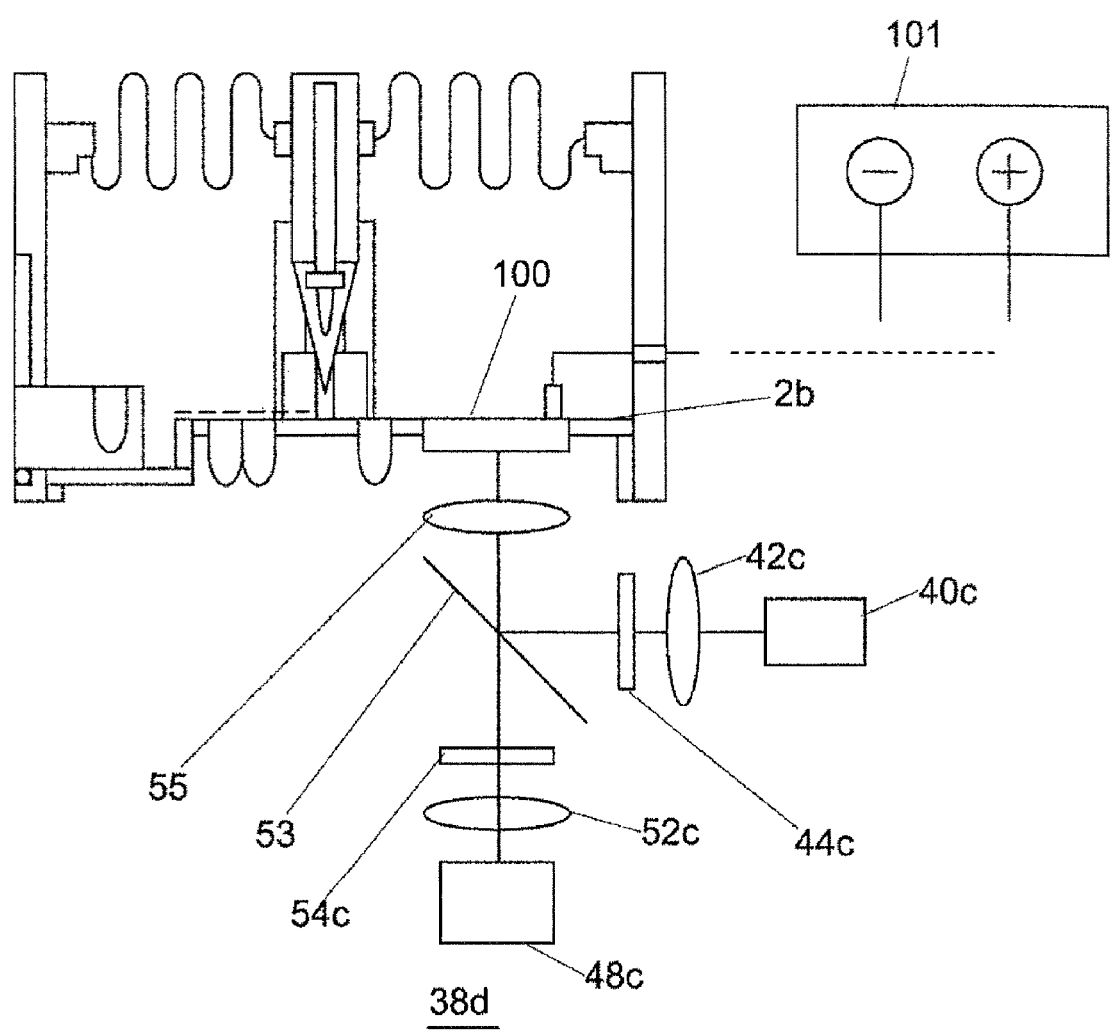
FIG. 11 is a vertical sectional view showing the reaction kit shown in FIG. 10A and an example of a detection unit used for the detection of a reaction product in the reaction kit according to the present invention.

The detection unit 38d is shown in FIG. 11. The detection unit 38d includes an excitation optical system and a fluorescence-receiving optical system to carry out fluorescence detection of sample components passing through a predetermined position in the electrophoretic separation channel 102. Since the detection unit 38d detects the fluorescence of sample components passing through a fixed position, it is not necessary to move the detection unit 38d.

The excitation optical system has a light source 40c, a lens 42c for condensing light emitted from the light source 40c to obtain parallel light, and a filter 44c provided on the optical path of parallel light beams obtained by the lens 42c to select light having a predetermined excitation wavelength from light emitted from the light source 40c.

The detection unit 38d further includes a dichroic mirror 53 and an objective lens 55 to irradiate a predetermined position in the electrophoretic separation channel 102 with excitation light obtained by the excitation optical system from the back surface side of the electrophoresis chip 100 and to receive fluorescence emitted from the position and convert it into parallel light. It is to be noted that the dichroic mirror 53 is designed so as to reflect light having an excitation wavelength to be used for the reaction kit and transmit light having a fluorescence wavelength.

The fluorescence-receiving optical system of the detection unit 38d is arranged at a position where it can receive fluorescence converted into parallel light by the objective lens 55 and passed through the dichroic mirror 53. The fluorescence-receiving optical system has a filter 54c for selecting light having a predetermined fluorescence wavelength from fluorescence passed through the dichroic mirror 53 and a lens 52c for condensing the fluorescence having a wavelength selected by the filter 54c to introduce condensed light into a detector 48c. As described above, the reason for once converting light into parallel light by the lenses 42c and 55 is to improve the precision of wavelength selection by the filters 44c and 54c.

In the case of using such a detection unit 38d, light having an excitation wavelength for exciting a reaction product is selected by the filter 44c from light emitted from the light source 40c to irradiate the reaction product passing through a predetermined position in the electrophoretic separation channel 102 with the light, and fluorescence emitted from the reaction product is received by the light-receiving optical system, and light having a predetermined fluorescence wavelength is selected by the filter 54c and detected by the photodetector 48c.

Figure 12A:
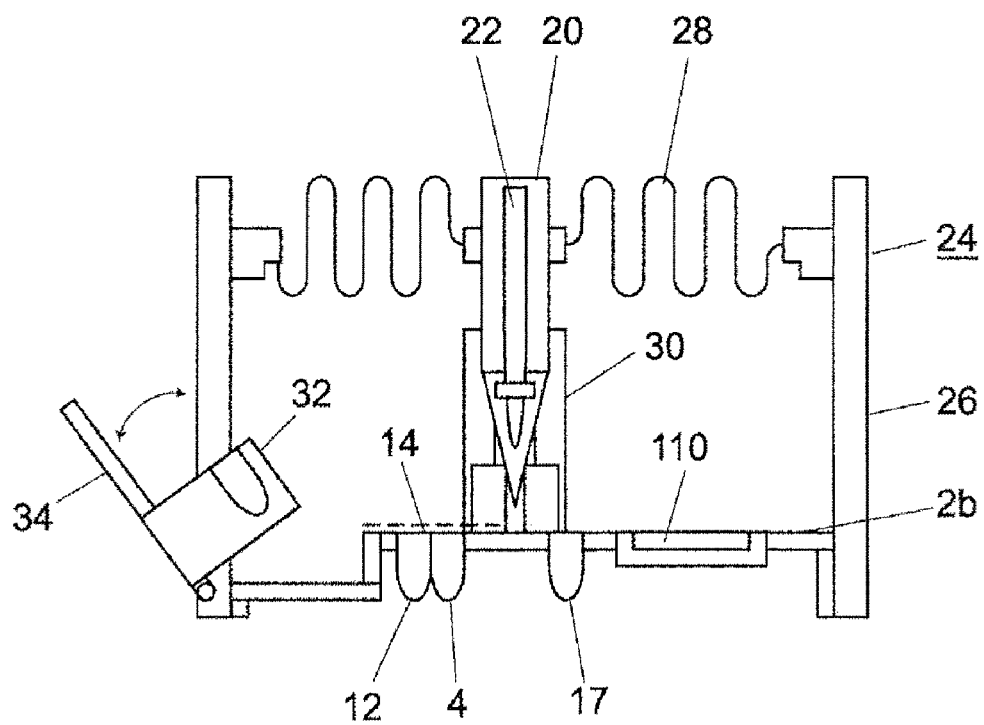
FIG. 12A is a vertical sectional view of another example of the reaction kit.
Figure 12B:
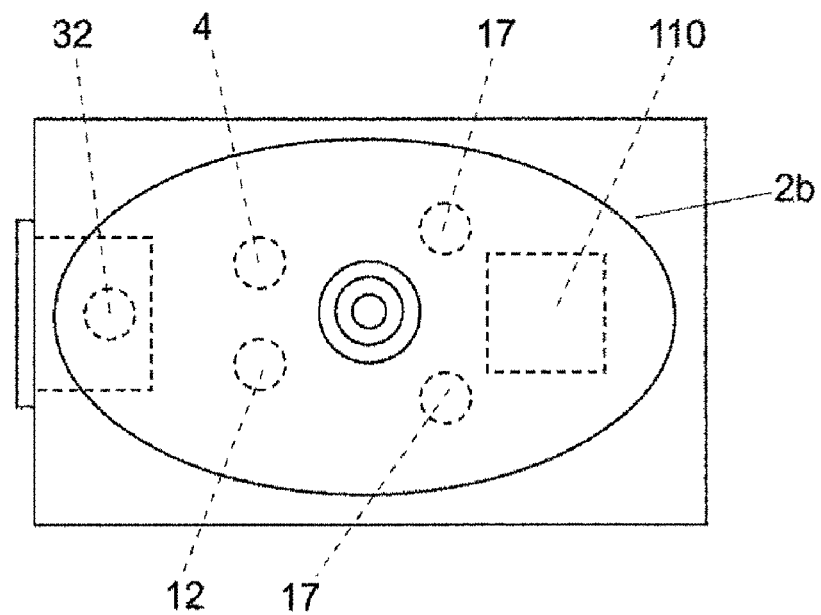
FIG. 12B is a plan view showing a reaction plate and a dispensation tip of the reaction kit shown in FIG. 12A.

A reaction plate 2b of the reaction kit shown in FIG. 12 has a DNA chip 110 as the analysis section. When a reaction product contains a gene, probes, which react with the gene, are immobilized to the DNA chip 110. The DNA chip 110 is subjected to fluorescence detection from the back surface side thereof, and is therefore made of a low self-fluorescence and an optically-transparent resin such as polycarbonate or glass.

The reaction plate 2b further has cleaning solution containers 17 formed in the top surface thereof. The cleaning solution containers 17 contain a cleaning solution for separating and removing the reaction product not having been bound to the probes from the reaction product having been bound to the probes in the DNA chip 110. Further, the cleaning solution containers 17 are sealed with a film through which the tip of the dispensation tip 20 can pass.

In a case where the reaction kit is used for gene analysis, the reagent container 12 is allowed to previously contain a PCR reaction reagent. In this case, the reaction container 4 serves as a PCR reaction container.

In a case where a gene sample is measured using the reaction kit, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is carried out by controlling the temperature of the mixture contained in the reaction container 4 according to a predetermined temperature cycle.

After the completion of the PCR reaction, an obtained reaction mixture is supplied as a sample from the reaction container 4 to the DNA chip 110 by the dispensation tip 20. After the completion of incubation, a cleaning solution is supplied from the cleaning solution container 17 to the DNA chip 110 by the dispensation tip 20, and then a reaction product not having been bound to the probes is removed by sucking the cleaning solution into the dispensation tip 20.

The reaction product having been bound to the probes can be detected by fluorescence by previously labeling the reaction product with a fluorescent material. The detection of the presence of fluorescence in the DNA chip 110 indicates that a gene corresponding to the probe immobilized at a position where fluorescence has been detected is contained in the sample.

In order to detect the reaction product having been bound to the probes in the DNA chip 110, the reaction kit treatment equipment includes a detection unit 38e.

Figure 13:
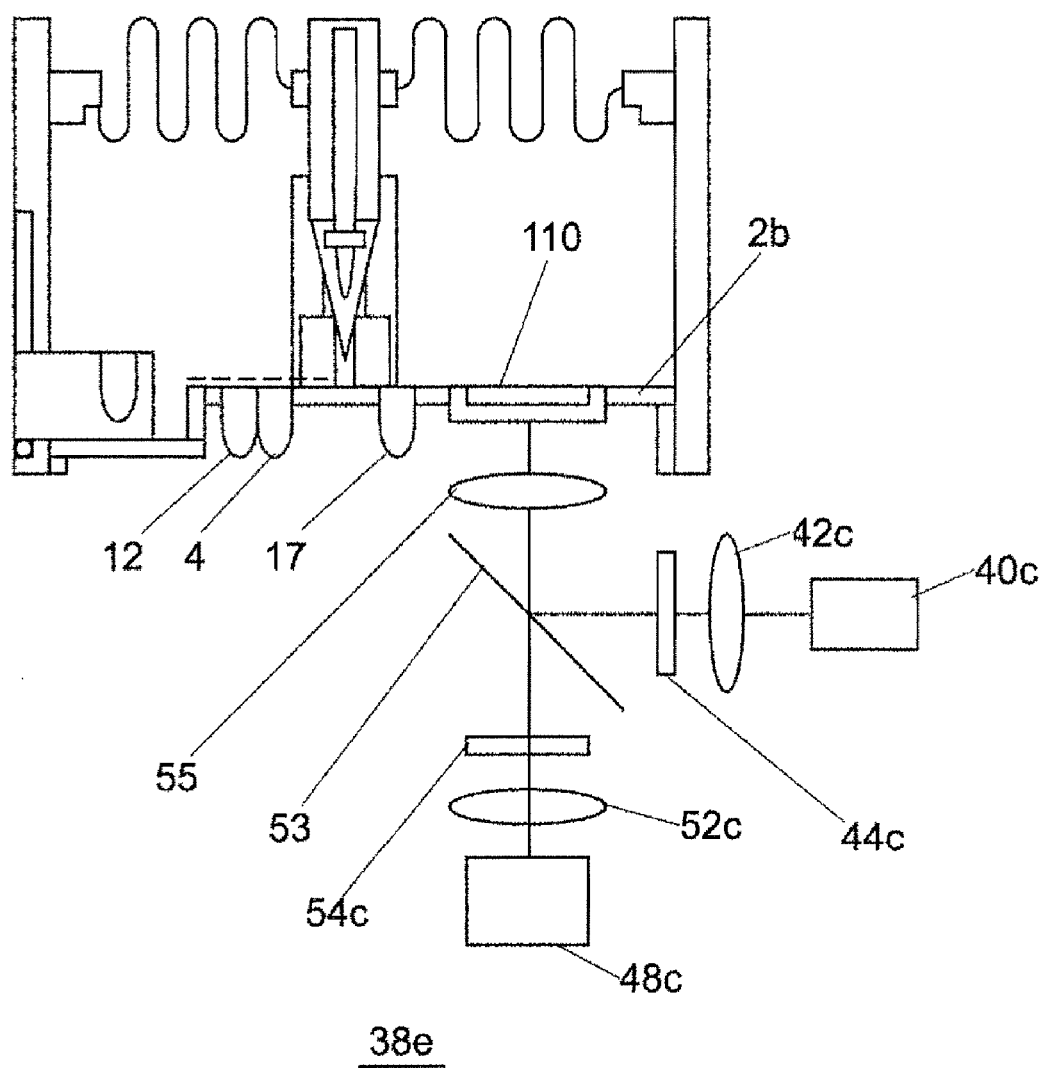
FIG. 13 is a vertical sectional view showing the reaction kit shown in FIG. 12A and an example of the detection unit used for the detection of a reaction product in the reaction kit according to the present invention.
Figure 20:
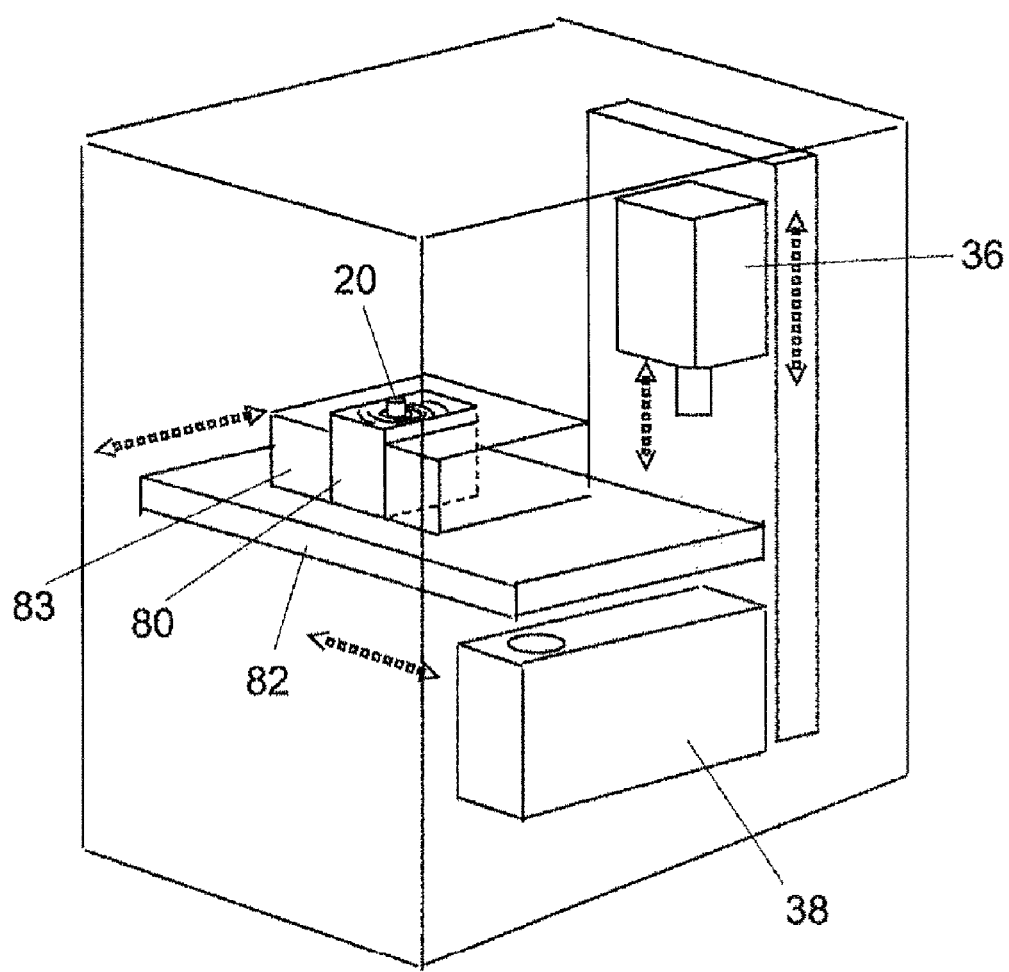
FIG. 20 is a perspective view schematically showing the interior structure of one embodiment of the reaction kit treatment equipment according to the present invention.

The detection unit 38e is shown in FIG. 13. The structure of an optical system of the detection unit 38e is the same as that of the detection unit 38d shown in FIG. 11, and therefore the description thereof is omitted. The detection unit 38e is different from the detection unit 38d shown in FIG. 11 in that it is movably supported so that fluorescence detection can be carried out for all the probes arranged in the DNA chip 110. Such detection can be achieved, as shown in FIG. 20, by allowing a table 82 to move in the X direction and by allowing the detection unit 38e to move in the Y direction.

Figure 14:
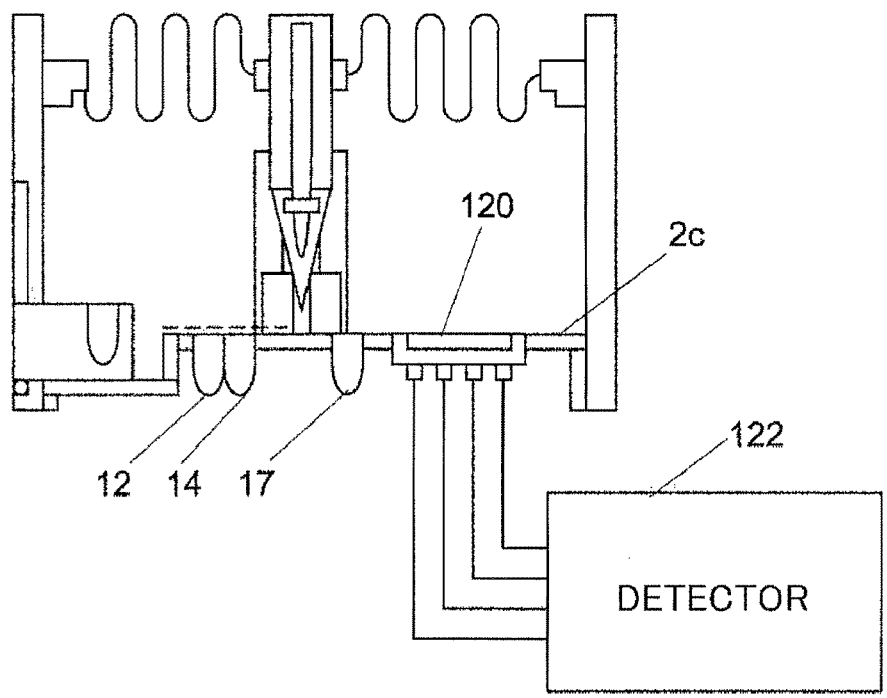
FIG. 14 is a vertical sectional view showing another example of the reaction kit and another example of the detection unit used for the detection of a reaction product in the reaction kit according to the present invention.

A reaction plate 2c of the reaction kit shown in FIG. 14 has a DNA chip 120 as the analysis section. The DNA chip 120 is different from the DNA chip 110 of the reaction kit shown in FIG. 12 in that it is designed to allow a reaction product to be detected not by fluorescence detection but by electric detection. The DNA chip 120 utilizes a phenomenon in which the current value of each probe varies depending on whether a sample gene has been bound to the probe or not. Since the DNA chip 120 is not subjected to optical detection, the material of the DNA chip 120 does not need to be optically transparent but needs to be electrically insulating.

When a reaction product contains a gene, probes, which react with the gene, are immobilized to the DNA chip 120. Each of the probes is connected to an electrode provided on the back surface of the reaction plate so that the current value thereof can be measured. In the case of using the reaction kit, it is not necessary to previously label a sample with a fluorescent material.

The electrodes provided on the back surface of the reaction plate and connected to the probes are connected also to a detector 122 provided in the reaction kit treatment equipment to measure the current value of each of the probes to detect the reaction product in the DNA chip 120.

The reaction plate 2c also has a cleaning solution container 17 formed in the top surface thereof. The cleaning solution container 17 contains a cleaning solution for separating the reaction product not having been bound to the probes immobilized to the DNA chip 120 from the reaction product having been bound to the probes and removing the former from the DNA chip 120. Further, the cleaning solution container 17 is sealed with a film through which the tip of the dispensation tip 20 can pass. The reagent container 12 previously contains a PCR reaction reagent. The reaction container 4 serves as a PCR reaction container.

In a case where a gene sample is measured by the reaction kit, the sample is introduced into the reaction kit from the sample container 32, and then the reaction kit is attached to the reaction kit treatment equipment. In the reaction kit treatment equipment, the sample contained in the sample container 32 is dispensed into the reaction container 4 by the dispensation tip 20, and then a PCR reaction reagent contained in the reagent container 12 is also dispensed into the reaction container 4 by the dispensation tip 20. Further, mineral oil (not shown) is layered onto a mixture of the sample and the reagent contained in the reaction container 4, and then PCR reaction is performed by controlling the temperature of the mixture contained in the reaction container 4 according to a predetermined temperature cycle.

After the completion of the PCR reaction, an obtained reaction mixture is supplied as a sample from the reaction container 4 to the DNA chip 120 by the dispensation tip 20. Then, a cleaning solution is supplied from the cleaning solution container 17 to the DNA chip 120 by the dispensation tip 20, and then a reaction product not having been bound to the probes is removed by sucking the cleaning solution into the dispensation tip 20.

In order to detect the reaction product having been bound to the probes in the DNA chip 120, the reaction kit treatment equipment includes a detector 122. After the reaction product not having been bound to the probes is removed, the current value of each probe is measured by the detector 122.

It is to be noted that a gene sample can be measured even when the DNA chip 110 or 120 of the reaction kit shown in FIG. 12 or 14 is replaced with a hybridization region.

Figure 15:
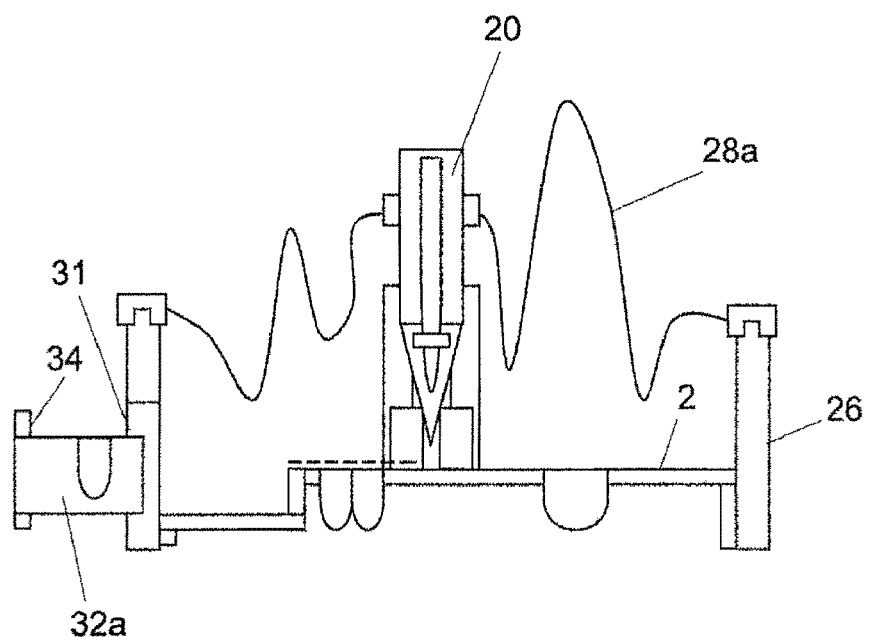
FIG. 15 is a vertical sectional view of another example of the reaction kit.

FIG. 15 shows another reaction kit different in the structure of the cover. More specifically, the reaction kit shown in FIG. 1 has a bellows film 28 as part of the cover movably supporting the dispensation tip 20 and covering a space above the reaction plate 2, but the reaction kit shown in FIG. 15 has a flexibly deformable film 28a as part of the cover. As in the case of the bellows film 28, the film 28a is preferably made of Nylon®, polyvinyl chloride, or a rubber material such as silicone rubber.

Further, the reaction kit shown in FIG. 15 is different from the reaction kit shown in FIG. 1 also in the structure of the sample container. More specifically, in the case of the reaction kit shown in FIG. 1, one side of the sample container is rotatably supported by the cover main body 26, but a sample container 32a of the reaction kit shown in FIG. 15 is slidably attached to the cover main body 26. Also, in the case of such a sample container 32a, a sample can be dispensed into the sample container 32a by pulling the sample container 32a toward the outside of the cover main body 26. The sample container 32a of the reaction kit shown in FIG. 15 is the same as the sample container 32 of the reaction kit shown in FIG. 1 in that the opening 31 of the cover main body 26 can be closed by sliding the sample container 32a toward the inside of the cover main body 26 and can be sealed by bringing the plate 34 into intimate contact with the cover main body 26 using a pressure-sensitive adhesive previously applied onto the inner surface of the plate 34 or by using a sealant.

The detection unit 38a, 38b, or 38c is arranged in the reaction kit treatment equipment so as to be located under the reaction plate 2 of the reaction kit attached to the treatment equipment.

Figure 16A:
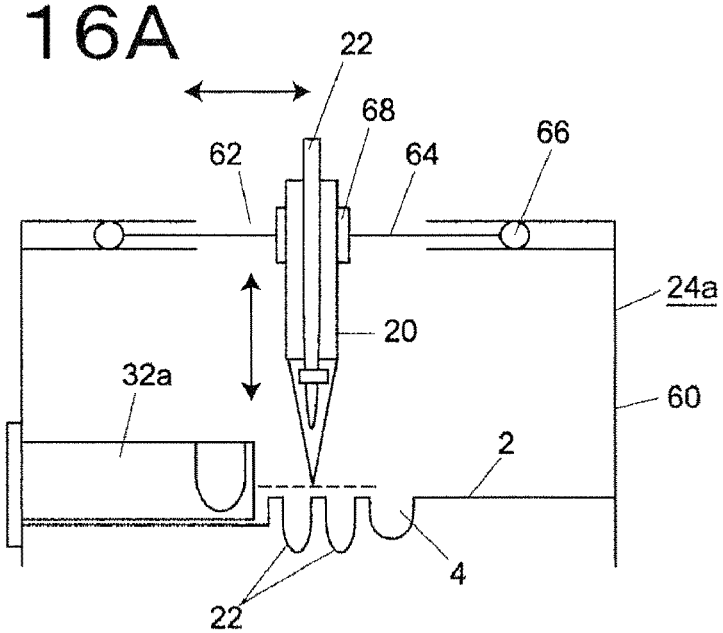
FIG. 16A is a vertical sectional view of another example of the reaction kit.
Figure 16B:
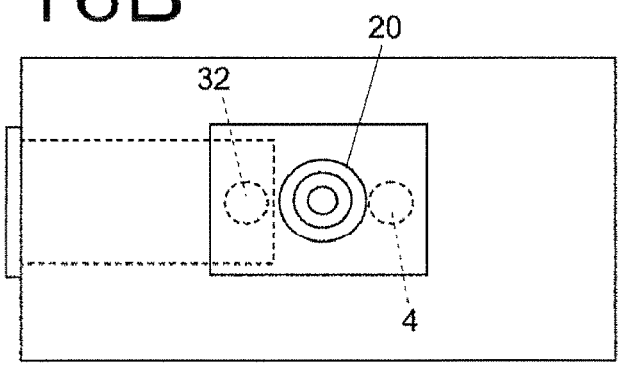
FIG. 16B is a plan view showing a reaction plate and a dispensation tip of the reaction kit shown in FIG. 16A.
Figure 16C:
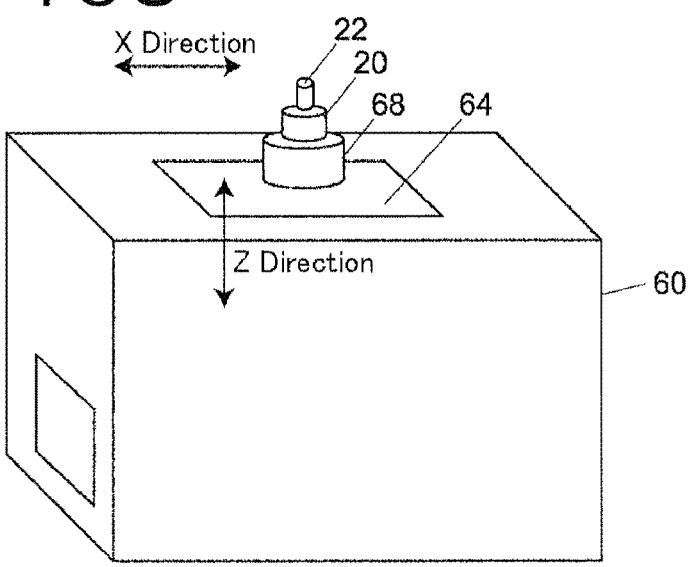
FIG. 16C is a perspective view showing the appearance of the reaction kit shown in FIG. 16A.

FIG. 16A shows another reaction kit, FIG. 16B is a horizontal sectional view of the reaction kit shown in FIG. 16A, and FIG. 16C is a perspective view showing the appearance of the reaction kit shown in FIG. 16A.

The reaction kit shown in FIG. 16 has a cover movably supporting the dispensation tip 20, and the cover is made of a material having stiffness. A cover main body 60 of a cover 24a has an opening 62 located above the reaction plate 2. In the opening 62, a cover plate 64 for movably supporting the dispensation tip 20 is provided so that the dispensation tip 20 can be moved within a range defined by the opening 62. A part of the cover main body 60 around the opening 62 has a double structure having an interior gap, and a sealant 66 is provided around the periphery of the cover plate 64. The sealant 66 is moved in the X direction in the interior gap of the double structure provided around the opening 62 of the cover main body 60, which allows the cover plate 64 to move in the X direction in a horizontal plane. Further, the dispensation tip 20 is supported by the cover plate 64 by means of another sealant 68, which is interposed between the dispensation tip 20 and the cover plate 64, so as to be able to slide in the vertical direction (Z direction).

In the reaction kit shown in FIG. 16, the cover plate 64 is moved in a horizontal plane while the reaction kit is kept hermetically sealed by a sealing structure constituted from the cover plate 64, the sealant 66, and the interior gap of the double structure provided in the upper part of the cover main body 60, and the dispensation tip 20 is moved in the vertical direction while the reaction kit is kept hermetically sealed by the sealant 68. This makes it possible to freely move the dispensation tip 20 in a space above the reaction plate 2 in two directions, i.e., in the vertical direction and a direction in a horizontal plane.

Figure 17A:
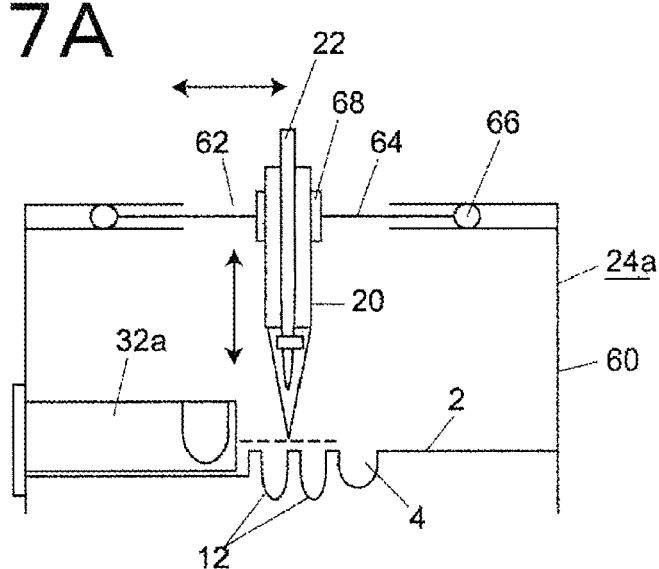
FIG. 17A is a vertical sectional view of another example of the reaction kit.
Figure 17B:
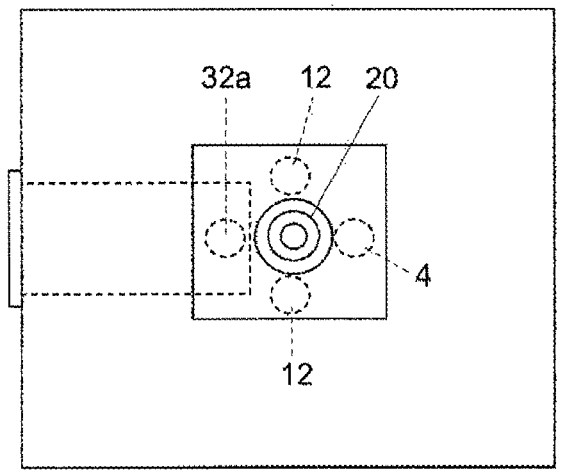
FIG. 17B is a plan view showing a reaction plate and a dispensation tip of the reaction kit shown in FIG. 17A.
Figure 17C:
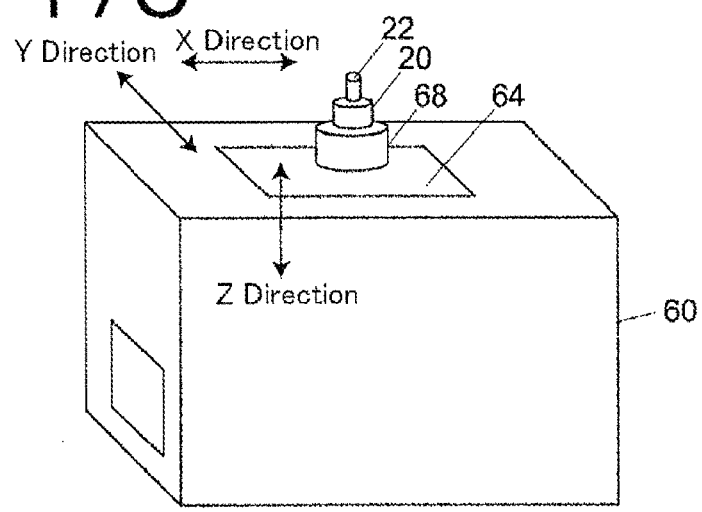
FIG. 17C is a perspective view showing the appearance of the reaction kit shown in FIG. 17A.

FIG. 17 shows another reaction kit. The reaction kit shown in FIG. 17 is the same as the reaction kit shown in FIG. 16 except that the cover plate 64 can be moved in two directions, i.e., X and Y directions, and that the number of the reagent containers 12 provided in the reaction plate 2 is increased.

Figure 18A:
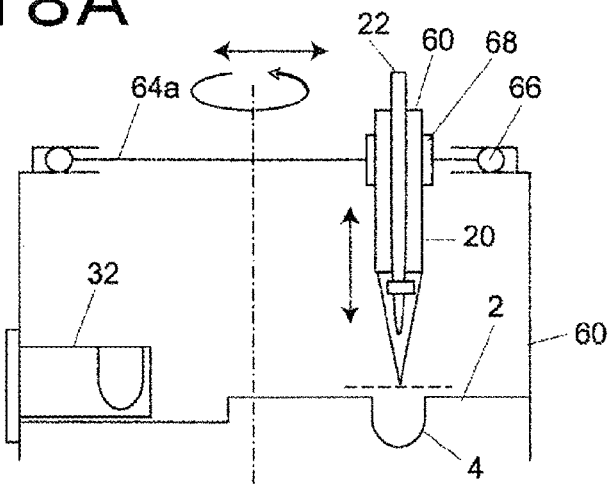
FIG. 18A is a vertical sectional view of another example of the reaction kit.
Figure 18B:
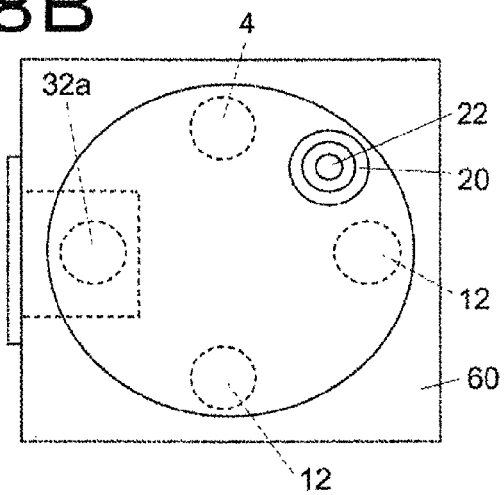
FIG. 18B is a plan view showing a reaction plate and a dispensation tip of the reaction kit shown in FIG. 18A.
Figure 18C:
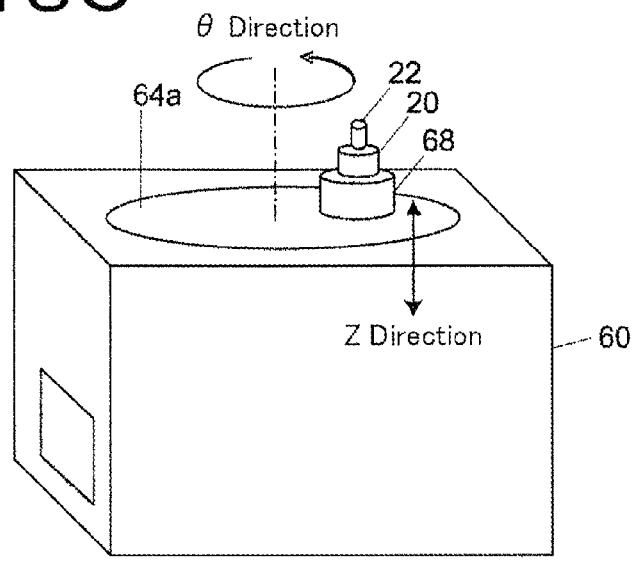
FIG. 18C is a perspective view showing the appearance of the reaction kit shown in FIG. 18A.

FIG. 18 shows another reaction kit. The reaction kit shown in FIG. 18 is different from the reaction kit shown in FIG. 16 in that a cover plate 64a as an upper member of the cover is supported so as to be able to rotate in the in-plane direction to move the dispensation tip 20 in the in-plane direction. The cover plate 64a has a disc shape, and the sealant 66 is attached to the periphery of the cover plate 64a. The sealant 66 is held in the interior gap of the double structure provided in the upper part of the cover main body 60, and rotatably supports the cover plate 64a while keeping the reaction kit hermetically sealed. The dispensation tip 20 is supported by the cover plate 64a by means of the sealant 68 so as to be able to move in the vertical direction. The dispensation tip 20 supported by the cover plate 64a is located off the center of rotation of the cover plate 64a.

By rotating the cover plate 64a, it is possible to move the dispensation tip 20 on the circumference of a circle whose center is the rotational center of the cover plate 64a. Therefore, the reaction container 4 and the reagent containers 12 provided in the reaction plate 2 and the sample container 32 are arranged so as to be located on the movement locus of the dispensation tip 20.

Figure 19A:
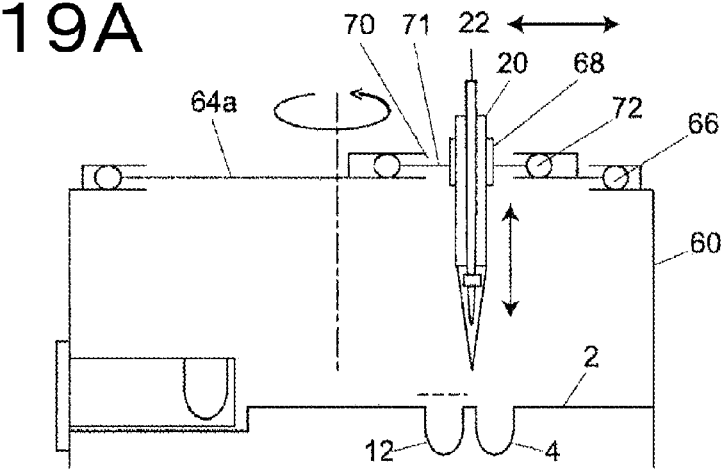
FIG. 19A is a vertical sectional view of another example of the reaction kit.
Figure 19B:
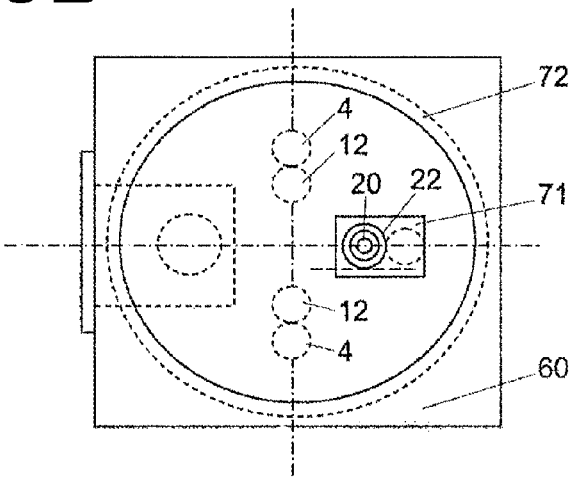
FIG. 19B is a plan view showing a reaction plate and a dispensation tip of the reaction kit shown in FIG. 19A.
Figure 19C:
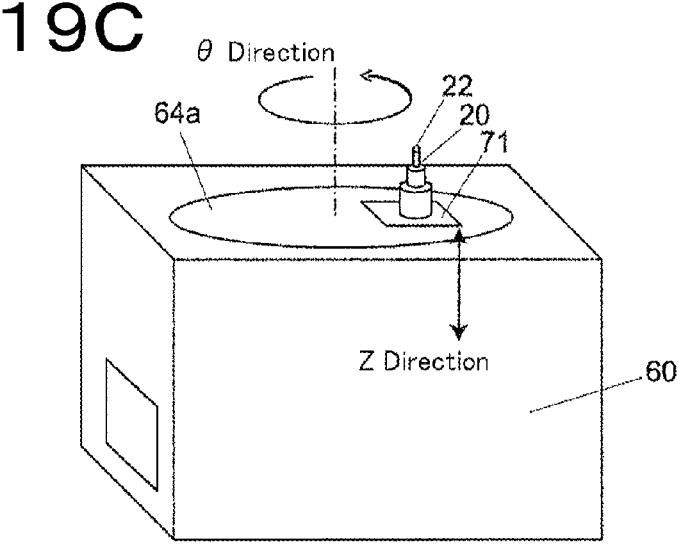
FIG. 19C is a perspective view showing the appearance of the reaction kit shown in FIG. 19A.

FIG. 19 shows another reaction kit. The reaction kit shown in FIG. 19 is different from the reaction kit shown in FIG. 18 in that the cover plate 64a also has an opening 70, a double structure having an interior gap is provided around the opening 70, and another cover plate 71 is movably supported by the double structure by means of a sealant 72 held in the interior gap of the double structure. The dispensation tip 20 is supported by the cover plate 71 by means of another sealant 68 so as to be able to move in the vertical direction.

The dispensation tip 20 can be moved also in the in-plane direction by the sealant 72. Therefore, the dispensation tip 20 can be moved within a range defined by both the circumference of a circle obtained by rotating the cover plate 64a and a horizontal plane obtained by moving the smaller cover plate 71 movable by the sealant 72, that is, within a doughnut-shaped range whose center is the rotational center of the cover plate 64a. In the case of the reaction kit shown in FIG. 19, the moving range of the dispensation tip 20 becomes larger, and therefore it is possible to increase the numbers of the reaction containers 4 and the reagent containers 12 arranged in the moving range of the dispensation tip 20. In addition, it is also possible to increase the degree of freedom of arrangement of these containers and the sample container 32.

FIG. 20 is a perspective view schematically showing the interior structure of one embodiment of the reaction kit treatment equipment according to the present invention.

The reference numeral 80 denotes the reaction kit described above. The reaction kit 80 is attached onto a table 82 provided as a reaction kit attachment section. The table 82 has an opening in its surface facing the lower surface of the reaction kit 80. Under the table 82, a detection unit 38 is arranged to optically detect a reaction product contained in the reaction container 4 of the reaction kit 82. On the table 82, a temperature control unit 83 is arranged to control the temperature of the reaction kit 82. In a case where gene amplification reaction is carried out in the reaction container 4 or a reaction container for gene amplification provided separately from the reaction container 4 of the reaction kit, the temperature control unit 83 is used to carry out temperature control for gene amplification reaction. Further, in a case where the reaction kit has an analysis section requiring temperature control, the temperature control unit 83 is used to carry out temperature control of the analysis section. The temperature control unit 83 may have both the function of carrying out temperature control for gene amplification reaction and the function of carrying out temperature control of the analysis section. The detection unit 38 shown in FIG. 20 generically denotes the detection means shown in FIGS. 7 to 9, 11, 13, and 14. The table 82 is moved in a forward-backward direction (X direction), and on the other hand, the detection unit 38 is supported so as to be able to move in a lateral direction (Y direction) orthogonal to the moving direction of the table 82. It is to be noted that the detection unit 38 may be fixed depending on a detection method used.

The drive unit 36 for driving the dispensation tip 20 is attached near the table 82 so as to be able to move in the Y and Z directions. As shown in FIG. 3, the drive unit 36 has a tip holding section 36a for holding the dispensation tip 20 by engaging with the proximal end of the dispensation tip 20 and a syringe drive section 36b for driving the syringe 22 by engaging with a plunger of the syringe 22 provided in the dispensation tip 20. The tip holding section 36a and the syringe drive section 36b are coaxially provided in the drive unit 36. Such a drive unit 36 allows both the movement of the dispensation tip 20 and the driving of the syringe 22 to be carried out.

Figure 21:
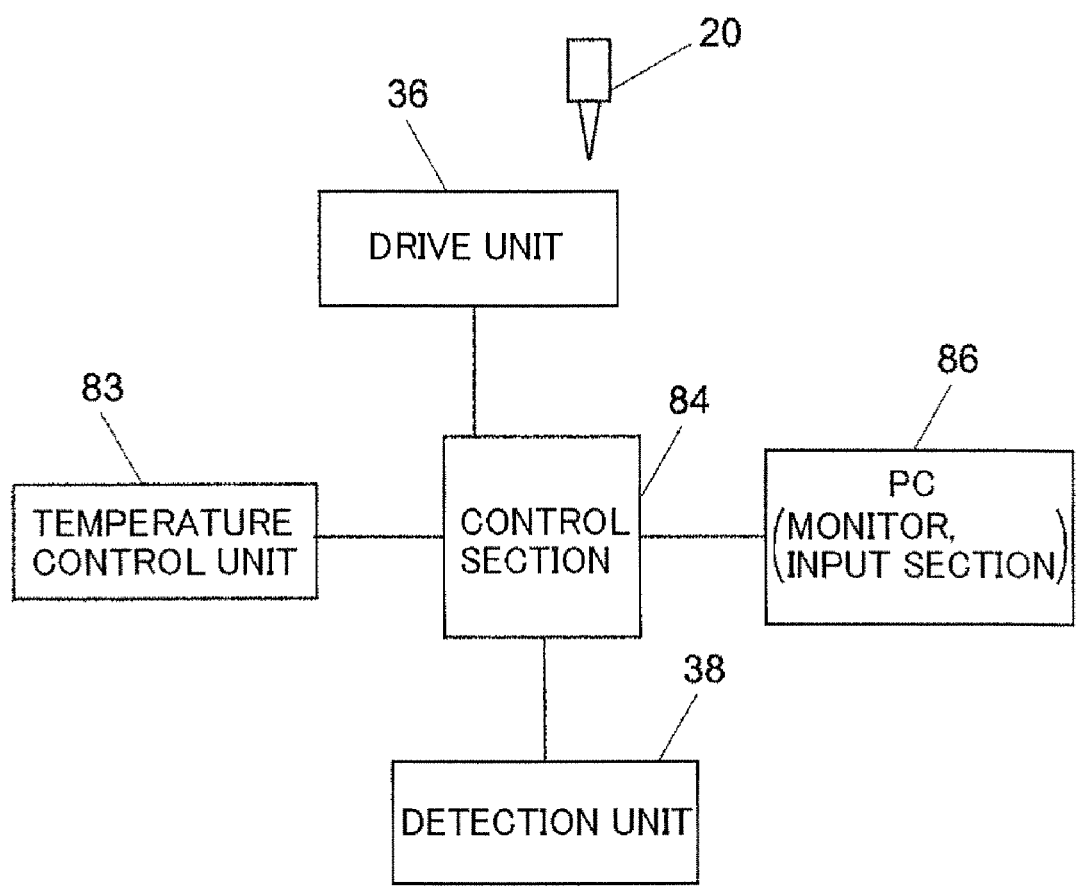
FIG. 21 is a block diagram showing the control system of the reaction kit treatment equipment shown in FIG. 20.

FIG. 21 is a block diagram showing the control system of the reaction kit treatment equipment according to the embodiment. The reaction kit treatment equipment includes a control section 84 for controlling the treatment of the reaction kit 80 attached to the table 82. The control section 84 is constituted from a dedicated purpose computer (CPU) or a general-purpose personal computer. The control section 84 controls the movement of the dispensation tip 20 driven by the drive unit 36 engaged with the proximal end of the dispensation tip 20, dispensation operation by the dispensation tip 20, temperature control carried out by the temperature control unit 83, and the operation of the detection unit 38 for optically detecting a reaction product by irradiating the reaction container 4 of the reaction kit 80 with measuring light or excitation light.

In order to use the control section 84 as an input section externally operated or a monitor for displaying detection results, an external computer such as a personal computer (PC) 86 may be connected to the control section 84.

INDUSTRIAL APPLICABILITY

The present invention can be applied to measurement of various chemical and biochemical reactions.

What is claimed is:

1. Reaction kit treatment equipment for treating a reaction kit,
the reaction kit comprising a reaction plate having at least a reaction container for carrying out the reaction of a sample, an airtight cover for covering a space above the top surface of the reaction plate, a sample container provided in the space, and a dispensation tip attached to and held movably by the cover and arranged so that a distal end side thereof is located inside the space covered with the cover and a proximal end thereof is located outside the space to transfer liquid over the reaction plate, the dispensation tip being supported movably in an in-plane direction parallel to the top surface of the reaction plate and in a direction perpendicular to the top surface,
wherein the airtight cover is fixed directly to the reaction plate so that the space is cut off from the outside environment,
wherein the airtight cover has a cover main body and an upper cover, the cover main body having stiffness to maintain the shape of the cover and being provided integrally with the reaction plate, the upper cover being attached to the cover main body so as to be arranged above the top surface of the reaction plate, being formed of an airtight and flexible material, and holding and movably supporting the dispensation tip,
wherein the upper cover is formed of a bellows film or a flexibly deformable film, allowing the movement of the dispensation tip by flexibly deforming of the film, and
wherein the dispensation tip has a syringe for carrying out dispensation operation or a filter in the tip portion thereof, the dispensation tip preventing entry of foreign matter from the outside of the space through the dispensation tip and preventing release of a reaction product into the outside of the space through the dispensation tip, the reaction kit treatment equipment comprising:
a reaction kit attachment section for attaching the reaction kit;
a drive unit having a tip holder for engaging detachably with the proximal end of the dispensation tip and moving and driving the dispensation tip between the sample container and the reaction container only within the space to carry out dispensing operation of the sample from the sample container to the reaction container with the dispensation tip being held by the cover;
means for detecting a reaction product in the reaction plate; and
a control section for controlling at least the dispensation operation carried out by the drive unit and the detection operation carried out by the detection means.

2. The reaction kit treatment equipment according to claim 1,
the reaction plate requiring temperature control during reaction or analysis,
the reaction kit treatment equipment further comprising a temperature control unit for controlling the temperature of the reaction plate.

3. The reaction kit treatment equipment according to claim 1, wherein the detection means comprises an absorbance detector provided with an irradiation optical system for irradiating a reaction product with measuring light from the outside of the reaction plate, and a light-receiving optical system for receiving and detecting the measuring light absorbed by the reaction product.

4. The reaction kit treatment equipment according to claim 1, wherein the detection means comprises a fluorescence detector provided with an excitation optical system for irradiating a reaction product with excitation light from the outside of the reaction plate, and a light-receiving optical system for receiving and detecting fluorescence emitted from the reaction product excited by the excitation light.

5. The reaction kit treatment equipment according to claim 1, wherein the detection means comprises an emission detector provided with a light-receiving optical system arranged outside the reaction plate for receiving and detecting light emitted from a reaction product.

6. The reaction kit treatment equipment according to claim 1, wherein the reaction plate has an electrophoresis section for analyzing a reaction product by electrophoretic separation, and the detection means has a power supply for applying an electrophoresis voltage to the electrophoresis section and an optical detector for optically detecting the components of the reaction product separated by the electrophoresis section.

7. The reaction kit treatment equipment according to claim 1, wherein the reaction plate has a probe region where probes to be reacted with a gene are arranged to analyze a reaction product, and the detection means has an optical detector for optically detecting the components of the reaction product bound to the probes arranged in the probe region.

8. The reaction kit treatment equipment according to claim 1, wherein the reaction plate has a probe region where probes to be reacted with a gene are arranged to analyze a reaction product, and the detection means has a detector for electrically detecting the components of the reaction product bound to the probes arranged in the probe region.

* * * * *